United States Patent
Wei et al.

(10) Patent No.: US 9,127,304 B2
(45) Date of Patent: Sep. 8, 2015

(54) PROBE IMMOBILIZATION AND SIGNAL AMPLIFICATION FOR POLYMER-BASED BIOSENSOR

(75) Inventors: Fang Wei, Santa Monica, CA (US); Wei Liao, Santa Monica, CA (US)

(73) Assignee: The Regents of the University of California, Oakland, CA (US)

( * ) Notice: Subject to any disclaimer, the term of this patent is extended or adjusted under 35 U.S.C. 154(b) by 465 days.

(21) Appl. No.: 12/823,988

(22) Filed: Jun. 25, 2010

(65) Prior Publication Data

US 2010/0330706 A1 Dec. 30, 2010

Related U.S. Application Data

(60) Provisional application No. 61/220,490, filed on Jun. 25, 2009.

(51) Int. Cl.
*G01N 33/545* (2006.01)
*C12Q 1/68* (2006.01)

(52) U.S. Cl.
CPC ............ *C12Q 1/6804* (2013.01); *C12Q 1/6825* (2013.01)

(58) Field of Classification Search
None
See application file for complete search history.

(56) References Cited

U.S. PATENT DOCUMENTS

| | | | |
|---|---|---|---|
| 6,468,785 B1 * | 10/2002 | Wang et al. | 435/287.2 |
| 2004/0038307 A1 * | 2/2004 | Lee et al. | 435/7.1 |
| 2005/0266456 A1 * | 12/2005 | Williams et al. | 435/6 |
| 2006/0207878 A1 * | 9/2006 | Myung et al. | 204/403.09 |

OTHER PUBLICATIONS

Akimov et al., "Electron-hole exchange interaction in a negatively charged quantum dot," Phys. Rev. B, 2005, vol. 71, pp. 075326-1-075326-7.*
Sung et al., "A glucose oxidase electrode based on polypyrrole with polyanion/PEG/enzyme conjugate dopant," Biosensors & Bioelectronics, 2003, vol. 18, issue 10, pp. 1231-1239.*
Wei et al. "Electrochemical detection of low-copy number salivary RNA based on specific signal amplification with a hairpin probe," Nucl. Acids Res., 2008, 36(11): e65, pp. 1-7; published on line May 17, 2008.*
Genisphere 3DNA dendrimer Product Information retrieved from http://www.genisphere.com/about_3dna.html on Apr. 17, 2012.*
Fang Wei and Chih-Ming Ho, "Aptamer-based electrochemical biosensor for Botulinum neurotoxin," Anal. Bioanal. Chem., Apr. 2009, vol. 393, No. 8, pp. 1943-1948, Epub Feb. 24, 2009.*
Wei et al., "Bio/Abiotic interface constructed from nanoscale DNA dendrimer and conducting polymer for ultrasensitive biomolecular diagnosis", Small, 2009, 5(15), pp. 1784-1790.

* cited by examiner

*Primary Examiner* — Galina Yakovleva
(74) *Attorney, Agent, or Firm* — Riverside Law LLP

(57) ABSTRACT

The present invention provides methods of making polymer-based biosensors and the biosensors made by said methods, wherein the biosensors comprise conducting polymers and negatively charged nanoparticles comprising a capture moiety. The present invention also provides methods of detecting analytes in a solution by contacting the solution with said polymer-based biosensors.

10 Claims, 12 Drawing Sheets

SEQUENCE LISTING

```
<160> NUMBER OF SEQ ID NOS: 1

<210> SEQ ID NO 1
<211> LENGTH: 42
<212> TYPE: DNA
<213> ORGANISM: Homo sapiens

<400> SEQUENCE: 1
gagggttgct cagccctctt caaaaacttc tccacaaccc tc                    42
```

US 9,127,304 B2

PROBE IMMOBILIZATION AND SIGNAL AMPLIFICATION FOR POLYMER-BASED BIOSENSOR

CROSS-REFERENCES TO RELATED APPLICATIONS

This application claims priority to U.S. Provisional Application Ser. No. 61/220,490, filed on Jun. 25, 2009, which is incorporated herein by reference in its entirety.

REFERENCE TO A "SEQUENCE LISTING," A TABLE, OR A COMPUTER PROGRAM LISTING APPENDIX SUBMITTED ON A COMPACT DISK

NOT APPLICABLE

STATEMENT AS TO RIGHTS TO INVENTIONS MADE UNDER FEDERALLY SPONSORED RESEARCH OR DEVELOPMENT

This invention was made with Government support of Grant Nos. DE015018 and DE 017790 awarded by the National Institutes of Health. The Government has certain rights in this invention.

BACKGROUND OF THE INVENTION

Signal transduction from the biological world to physical domain, or vice versa, is a common and challenging task. For example, if in vivo neural signals can be successfully read out through an array of probes, a much better understanding of neural networks' function can be obtained (Velliste, M. et al., *Nature, doi:*10.1038/*nature*06996 (2008); Cui, X. et al., *Journal of Biomedical Materials Research,* 56:261-272 (2001)). Additionally, if suitable multiple control signals can be fed into neural networks, muscle motion control in disabled patients will be only one of many exciting applications (Velliste, M. et al., *Nature, doi:*10.1038/*nature*06996 (2008); Nakagawa, H. et al., *Circulation,* 91:2264-2273 (1995)).

The signal transduction efficiency between the biological world and engineering devices critically depends on the bio/abiotic interface. Various methods have been reported for constructing the interface to facilitate signal transductions. Functional biomolecules can be immobilized onto self-assembled monolayers (SAMs) on silicon, gold, or polymer through direct chemical bonding (Gu, F. et al., *Proceedings of the National Academy of Sciences of the United States of America,* 105:2586-2591 (2008); Sieval, A. B. et al., *Langmuir,* 14:1759-1768 (1998); Linford, M. R. et al., *Journal of the American Chemical Society,* 117:3145-3155 (1995); Bertilsson, L. and Liedberg, B., *Langmuir,* 9:141-149 (1993)) or indirect binding of biopolymers, such as streptavidin (Lahiri, J. et al., *Langmuir,* 15:2055-2060 (1999); Peluso, P. et al., *Analytical Biochemistry,* 312:113-124 (2003)) and protein G (Caruso, F. et al., *Langmuir,* 13:3427-3433 (1997); Bieri, C. et al., *Nature Biotechnology,* 17:1105-1108 (1999)). A thin film of biopolymer is commonly used to increase the affinity and stability of immobilized biomolecules (Tharanathan, R. N. and Kittur, F. S., *Critical Reviews in Food Science and Nutrition,* 43:61-87 (2003); Tan, W. and Desai, T. A., *Biomedical Microdevices,* 5:235-244 (2003)). Among these materials, conducting polymer (CP) is extensively applied as an easily fabricated and biocompatible support material for a diverse array of analytes (Cosnier, S., *Analytical Letters,* 40:1260-1279 (2007); Cosnier, S., *Biosensors & Bioelectronics,* 14:443-456 (1999); Gerard, M. et al., *Biosensors & Bioelectronics,* 17:345-359 (2002); Ramanavicius, A. et al., *Electrochimica Acta,* 51:6025-6037 (2006); Sargent, A. et al., *Journal of Electroanalytical Chemistry,* 470:144-156 (1999); Fan, C. H. et al., *Proceedings of the National Academy of Sciences of the United States of America,* 100:6297-6301 (2003)).

Currently, most of the existing CP-based biosensors incorporate biomolecular probes, such as a oligonucleotide, antibody, or enzyme, directly into the polymer film by mixing them with monomer solution immediately before electropolymerization (Wang, J. and Jiang, M., *Langmuir,* 16:2269-2274 (2000); Ateh, D. D. et al., *Journal of the Royal Society Interface,* 3:741-752 (2006); Liao, W. and Cui, X. T., *Biosensors & Bioelectronics,* 23:218-224 (2007)). In some cases, the addition of anionic surfactant helps to increase the immobilization efficiency, as the biomolecules will not suffer from denaturation of chemical bonding and can be immobilized through a single-step fabrication procedure. However, highly efficient immobilization for a variety of biomolecular probes requires all the parameters (i.e. voltage or current for electropolymerization and concentration of monomer and probes) to be individually optimized if any change happens.

Therefore, a universal platform for immobilizing most types of probes with high surface density and high binding activity is desirable. The present invention addresses this need and others.

BRIEF SUMMARY OF THE INVENTION

In one aspect, the present invention provides a method of making a polymer-based biosensor, the method comprising the steps of (a) doping a solution of monomeric units of a conducting polymer with negatively charged nanoparticles comprising a capture moiety; and (b) polymerizing the monomeric units on the surface of the sensor comprising an electrode, thereby trapping the nanoparticles on the surface of the sensor.

In one embodiment, the method further comprises the step of (c) contacting the polymerized surface with a biological polymer of interest conjugated to a target moiety, wherein the target moiety has affinity for said capture moiety.

In one embodiment, the sensor comprises gold.

In one embodiment, the conducting polymer is selected from the group consisting of a poly(acetylene), a poly(pyrrole), a poly(thiophene), a poly(aniline), a poly(p-phenylene sulfide), and a poly(para-phenylene vinylene). In one embodiment, the conducting polymer is a poly(pyrrole). In one embodiment, the monomeric units is pyrrole.

In one embodiment, the pyrrole is present at a concentration of between about 1 mM and about 100 mM. In one embodiment, the pyrrole is present at a concentration of between about 5 mM and about 20 mM.

In one embodiment, the charged nanoparticle comprises a negatively charged dendrimer. In one embodiment, the dendrimer is a DNA dendrimer.

In one embodiment, the charged nanoparticle is present at a concentration of between about 0.1% (v/v) and about 1.0% (v/v). In one embodiment, the surface density of the nanoparticles on the surface of the sensor is between about 0.20 pmol/cm$^2$ to about 2.0 pmol/cm$^2$.

In one embodiment, the capture moiety is an antibody or functional fragment thereof, an avidin, a streptavidin, an aptamer, a spiegelmer, a glutathione, or an S-peptide. In one embodiment, the capture moiety is an anti-biotin antibody or a streptavidin.

In one embodiment, polymerization is achieved by electropolymerization or photopolymerization. In one embodiment, a cyclic square-waveform electrical field is used for electropolymerization.

In one embodiment, the biological polymer of interest is a protein. In one embodiment, the biological polymer of interest is a nucleic acid.

In one embodiment, the target moiety is biotin.

In another aspect, the present invention provides a polymer-based biosensor made by a method of the present invention. In one embodiment, the conducting polymer of the polymer-based biosensor is a poly(pyrrole) and the nanoparticles are DNA dendrimers.

In yet another aspect, the present invention provides a method of detecting an analyte in a solution, the method comprising the steps of (a) contacting the solution with a polymer-based biosensor; (b) applying a voltage to the electrode; and (c) determining the current generated on the biosensor.

In one embodiment, the analyte is a protein. In one embodiment, the protein is present at a concentration of between about 100 fg/mL to about 2.5 µg/mL.

In one embodiment, the analyte is a nucleic acid. In one embodiment, the nucleic acid is present at a concentration of between about 10 aM to about 10 pM.

In one embodiment, the solution comprises a bodily fluid. In one embodiment, the bodily fluid is saliva.

In one embodiment, the analyte is an oral cancer biomarker. In one embodiment, the analyte is selected from the group consisting of IL-8 protein, IL-1β protein, and IL-8 mRNA.

DETAILED DESCRIPTION OF THE INVENTION

I. Introduction

Figure 1:
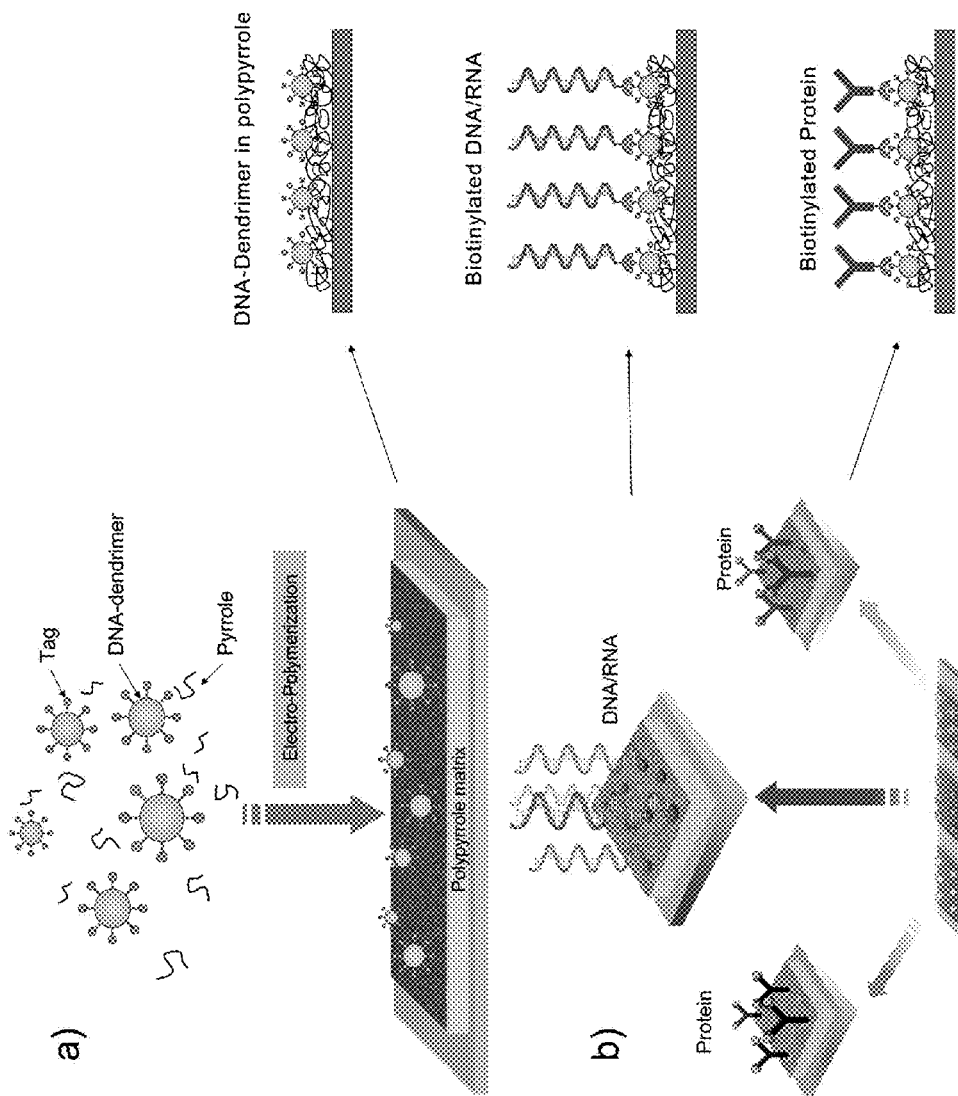
FIG. 1. Formation and use of DNA dendrimer-poly(pyrrole) biosensor. Schematic process of (A) DNA dendrimer-poly(pyrrole) (DDPpy) formation and (B) its application in the DDPpy-directed multiplexing immobilization of biomolecules.

The present invention provides polymer-based biosensors for probe immobilization and signal amplification, methods of making the polymer-based biosensors, and methods of detecting analytes using the polymer-based biosensors. As described herein, the combination of abiotic polymer substrate and biomolecule generates a biocompatible and widely applicable interface for detectors with multiple applications. Moreover, the bio/abiotic interface of the polymer-based biosensors of the present invention greatly improves the signal transduction process as compared to sensors with interfaces of abiotic nanoparticles and abiotic polymer, as measured by the improved limit of detection that is possible with the present invention.

The polymer-based biosensors of the present invention provide the advantage of a universal, pre-optimized platform for the immobilization of different types of probes, such that changing from one type of probe to another does not require changing the parameters of immobilization. The polymer-based biosensors of the present invention also provide the advantage of a precisely controllable surface density of immobilized probe, such that it is possible to easily determine how many probes are on the surface of the biosensor. Additionally, the polymer-based biosensors of the present invention provide the advantage of being compatible with, and being sensitive for, numerous types of surface detection techniques.

II. Definitions

As used herein, the following terms have the meanings ascribed to them unless specified otherwise.

As used herein, the term "biosensor" refers to a device that detects a target biological or chemical substance, condition, or reaction through the use of a biomolecule and transmits information about the biological or chemical substance, condition, or reaction as a signal. The term "biomolecule" as used herein indicates substance, compound, or component associated with a biological environment including, but not limited to, sugars, amino acids, peptides, proteins, oligonucleotides, polynucleotides, polypeptides, organic molecules, haptens, epitopes, biological cells, parts of biological cells, vitamins, hormones and the like. Various types of biosensors exist, such as electrochemical biosensors, colorimetric biosensors, optical biosensors, and thermal biosensors. In some embodiments, a biosensor of the present invention comprises an electrochemical biosensor, which comprises an electrode having a surface onto which a biomolecule is immobilized and which transmits information about a biological or chemical substance, condition, or reaction as an electrical signal. A biomolecule may be immobilized on the surface of the sensor by direct chemical bonding or by indirect bonding through a polymer film that is applied to the surface of the sensor. In some embodiments, a biomolecule may be immobilized to the surface of the sensor by directly incorporating the biomolecule into the polymer film to be applied to the surface.

As used herein, the term "conducting polymer" refers to a polymer that conducts electricity. A conducting polymer, as used herein, is applied to the surface of a sensor comprising an electrode. Types of conducting polymers suitable for the present invention include, but are not limited to, poly(acetylene)s, poly(pyrrole)s, poly(thiophene)s, poly(terthiophene)s, poly(aniline)s, poly(fluorine)s, poly(3-alkylthiophene)s, polytetrafluvalenes, polynapthalenes, poly(p-phenylene sulfide)s, and poly(para-phenylene vinylene)s. As used herein, the term conducting polymer also refers to modified variants of any of the conducting polymers described herein.

As used herein, the term "nanoparticle" refers to a defined particle of typically 5 to 5000, or more typically 5 to 500 atoms. Typical dimensions of the nanoparticles of the present invention are on the scale of a few nanometers, and can be tens of nanometers. The nanoparticles of the present invention typically have dimensions of less than 150 nanometers. In some embodiments, nanoparticles may be made from such materials as metal, such as silver or gold; semiconductor material; or carbon. In some embodiments, nanoparticles may be made from biological materials such as nucleic acids or peptides. In some embodiments, nanoparticles comprise DNA dendrimers. "DNA dendrimer," as used herein, refers to a monomer of deoxyribonucleic acid (DNA) having two strands of DNA, wherein a portion of one DNA strand binds to a portion of the other DNA strand to form a stable double strand and wherein the remaining portion of each DNA strand is single-stranded and available for modification (e.g, by labeling with any of a diverse range of molecules such as fluorophores, biotins, streptavidins, antibodies, aptamers or enzymes) or subsequent hybridization with a target nucleic acid sequence.

A nanoparticle of the present invention comprises a "capture moiety," which, as used herein, refers to any molecule that can specifically bind to or be bound by a target moiety on a biological polymer of interest. In some embodiments, the capture moiety may be directly bound to the nanoparticle or indirectly bound via a linker. In some embodiments, a capture moiety of the present invention comprises an oligonucleotide; a polypeptide; an antibody or a functional fragment thereof; an avidin; a streptavidin; an aptamer; Spiegelmer™ (a L-RNA aptamer); a glutathione; or an S-peptide. As a non-limiting example, a nanoparticle comprising a DNA dendrimer may comprise capture moieties comprising streptavidin molecules and/or anti-biotin antibodies bound to its single-stranded DNA.

As used herein, a "biological polymer" refers to any polynucleotide, polypeptide, or polysaccharide that is capable of binding to or reacting with a biological or chemical molecule of interest. In some embodiments, the biological polymer is an oligonucleotide, protein, antibody, or aptamer that is capable of binding a biomarker of interest. In some embodiments, the biomarker of interest is a protein or nucleic acid marker for the detection of a cancer, a viral infection, a bacterial infection, and/or any disease state for which diagnostic biomarkers have been identified. In some embodiments, the biomarker of interest is a protein or nucleic acid marker for the detection of an oral disease. "Oral disease" refers to diseases of the mouth, gums, throat, neck, lips, etc., including without limitation, oral cancers, aggressive, chronic, or necrotizing periodontal disease, gingivitis, gum disease, mouth, throat, or tongue ulcers, angular cheilitis, oral lichen planus, and the like. In some embodiments, the biomarker is IL-8 (GenBank Accession Number NM_000584) or IL-1β (GenBank Accession Number M15330).

The biological polymer of interest is conjugated to a target moiety. As used herein, the term "target moiety" refers to any molecule that can bind to or be bound by a capture moiety of a nanoparticle on the surface of a biosensor. As a non-limiting example, where the capture moiety of a nanoparticle comprises an antibody or functional fragment thereof, a suitable target moiety would be any antigen to which the antibody or functional fragment thereof can bind. Optionally, the biological polymer may also be labeled with a label or a detectable moiety. A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

As used herein, the terms "protein," "peptide," and "polypeptide" are used interchangeably herein to refer to a polymer of two or more amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

As used herein, the term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, ÿ-carboxyglutamate, and O-phosphoserine. Amino acid analogs refers to compounds that have the same basic chemical structure as a naturally occurring amino acid, i.e., an ÿ carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As used herein, the term "nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

As used herein, the term "analyte" is a substance that can be detected or measured using the polymer-based biosensor of the present invention. An analyte may comprise any biological or chemical molecule of interest, including but not limited to proteins, nucleic acids, vitamins, metabolites, metal ions, toxins, etc. An analyte may be obtained from any biological sample, including blood, saliva, tissue, cultured cells (e.g., primary cultures, explants, and transformed cells), stool, urine, etc. A biological sample is typically obtained from a eukaryotic organism, e.g., *C. elegans*, most preferably a mammal such as a primate e.g., chimpanzee or human; cow; dog; cat; a rodent, e.g., guinea pig, rat, mouse; or a rabbit.

III. Polymer-Based Biosensors

In one aspect, the present invention provides for polymer-based biosensors comprising a sensor comprising an electrode, wherein a conducting polymer and a negatively charged nanoparticle comprising a capture moiety are polymerized on the surface of the sensor. In some embodiments, the polymer-based biosensor may further comprise a biological polymer of interest conjugated to a target moiety, wherein the target moiety has high affinity for the capture moiety.

In some embodiments, the sensor is an electrochemical sensor. Typically, the sensor comprises two, three, or more electrodes. In some embodiments, a three electrode system, comprising a working electrode, a counter electrode, and a reference electrode, is used. In some embodiments, the sensor comprises an array of at least two three-electrode systems, more typically from about 10 to about 30 three-electrode systems, and optionally 100 or more three-electrode systems. The array of sensors can be formed on an integrated circuit using semiconductor technology methods, an example of which is disclosed in PCT Patent Publication No. WO99/08105, entitled "Techniques and Systems for Analyte Detection," published Feb. 19, 1999, and incorporate herein by reference. The sensor may comprise any conducting or semi-conducting material, including but not limited to noble metals (e.g., ruthenium, rhodium, palladium, silver, osmium, iridium, platinum, and gold), indium tin oxide, and silicon.

Polymerized on the surface of the sensor are a conducting polymer and a negatively charged nanoparticle comprising a capture moiety. The conducting polymer can be any polymer that is capable of conducting electricity and is biocompatible with biological species. Various classes of suitable conducting polymers are well known in the art and include, for example, poly(acetylene)s, poly(pyrrole)s, poly(thiophene)s, poly(terthiophene)s, poly(aniline)s, poly(fluorine)s, poly(3-alkylthiophene)s, polytetrafluvalenes, polynapthalenes, poly (p-phenylene sulfide)s, and poly(para-phenylene vinylene)s. Factors for determining whether a conducting polymer is suitable for the present invention include polymer thermal and environment stability, solubility, processivity, and conductivity when doped. These characteristics have been well-studied for different classes of conducting polymers and are known in the art. See, e.g., Shim et al., *J. Electrochem. Soc.* 137:538-544 (1990); Shim et al., Synth. Met. 29:E169-E174 (1989); Park et al., *J. Elrctrochem. Soc.* 140:2749-2752 (1993); Park et al., *J. Elrctrochem. Soc.* 140:609-614 (1993); Shim et al., *J. Elrctrochem. Soc.* 144:3027-3033 (1997). In some embodiments, the conducting polymer is poly(pyrrole) or poly-3,4-ethylenedioxythiophene (PEDOT).

Monomeric units of the conducting polymer are doped with a nanoparticle comprising a capture moiety before electropolymerization on the surface of the sensor. In some embodiments, the nanoparticle comprises a metal (e.g., gold, silver, nickel, chromium, iron, zinc, rubidium, or platinum), a semiconductor material (e.g., silicon), a ceramic material (e.g., oxides, nitrides, and carbides), an organic material (e.g., carbon), a biological material, an inorganic material, and/or a polymer material. In some embodiments, the nanoparticle comprises a biomolecule. Suitable biomolecules of the present invention include, for example, sugars, amino acids, peptides, proteins, oligonucleotides, polynucleotides, polypeptides, organic molecules, haptens, epitopes, biological cells, parts of biological cells, vitamins, hormones and the like.

In some embodiments, the nanoparticle comprises a capture moiety. A capture moiety may be any molecule that specifically binds to or is bound by a target moiety on a biological polymer of interest. Exemplary capture moieties include oligonucleotides, polypeptides, antibodies or functional fragments thereof, avidins, streptavidins, biotins, aptamers, Spiegelmers™ (L-RNA aptamers), glutathiones, and S-peptides. Each nanoparticle may comprise a plurality of capture moieties. In some embodiments, the nanoparticle comprises about 5 to about 1000 capture moieties.

In an exemplary embodiment, the nanoparticle is a DNA dendrimer. Dendrimers are polymers of spherical or other three-dimensional shapes that have precisely defined compositions and that possess a precisely defined molecular weight. Dendrimers can be synthesized as water-soluble macromolecules through appropriate selection of internal and external moieties. See, U.S. Pat. Nos. 4,507,466 and 4,568,737, incorporated by reference herein. Alternatively, DNA dendrimers are commercially available. The first well-defined, symmetrical, dendrimer family was the polyamidoamine (PAMAM) dendrimers, which are manufactured by the Dow Chemical Company. Since the synthesis and characterization of the first dendrimers, a large array of dendrimers of diverse sizes and compositions has been prepared. See, for example, Liu M. and Frechet J. M. J., *Pharm. Sci. Tech. Today* 2(11): 393 (1999).

A capture moiety may be an inherent component of a nanoparticle (e.g., a nanoparticle that is an oligonucleotide), or alternatively, a capture moiety may be a moiety that is directly or indirectly attached to the nanoparticle via a linker. Various types of linkers are known in the art, including but not limited to straight or branched-chain carbon linkers, heterocyclic carbon linkers, peptide linkers, and polyether linkers. For example, poly(ethelyne glycol) linkers are available from Shearwater Polymers, Inc., Huntsville, Ala. These linkers optionally have amide linkages, sulfhydryl linkages, or heterofunctional linkages.

A bifunctional linker having one functional group reactive with a group on one molecule (e.g., a capture moiety), and another group reactive on the other molecule (e.g., a nanoparticle), can be used to form the desired conjugate. Alternatively, derivatization can be performed to provide functional groups. Thus, for example, procedures for the generation of free sulfhydryl groups on peptides are also known (See U.S. Pat. No. 4,659,839). A linker may alternatively comprise a heterobifunctional crosslinker comprising two or more different reactive groups that form a heterocyclic ring that can interact with a capture moiety. For example, a heterobifunctional crosslinker such as cysteine may comprise an amine reactive group and a thiol-reactive group can interact with an aldehyde on a derivatized targeting molecule. Additional combinations of reactive groups suitable for heterobifunctional crosslinkers include, for example, amine- and sulfhydryl reactive groups; carbonyl and sulfhydryl reactive groups; amine and photoreactive groups; sulfhydryl and photoreactive groups; carbonyl and photoreactive groups; carboxylate and photoreactive groups; and arginine and photoreactive groups.

The conducting polymer and nanoparticle are polymerized on the surface of the sensor, thereby trapping or immobilizing the nanoparticles on the surface of the sensor. Typically, the conducting polymer and nanoparticle are pre-mixed before polymerization on the surface of the sensor. A solution of monomeric units of a conducting polymer is "doped" with nanoparticles (i.e., nanoparticles are added to the solution of monomeric units of a conducting polymer) immediately before polymerization onto the surface of the sensor. Optionally, an anionic surfactant may be added to the mixture to increase immobilization efficiency of the nanoparticle.

The surface morphology and surface density of the binding sites, or capture moieties, on the surface of the sensor will affect the performance of surface-immobilized molecular sensors. Specifically, sparsely distributed nanoparticles result in a low number of binding targets, whereas very crowded sensor surfaces restrict the recognition process between capture moiety and target moiety because of the limited free space. Therefore, the sensitivity of the biosensor for a target molecule can be adjusted by varying the surface density and surface morphology of the capture moieties on the surface of the sensor. The surface density of the nanoparticles, and the corresponding surface density of the binding sites of the nanoparticles, is directly proportional to the concentration of the nanoparticle in the conducting polymer matrix. Accordingly, the surface density of the binding sites, or capture moieties, on the surface of the sensor can be adjusted by varying the concentration of monomer units in the solution and by varying the concentration of nanoparticle in the solution. In some embodiments, the concentration of monomer units of conducting polymer is from about 1 mM to about 100 mM. In some embodiments, the concentration of monomer units of conducting polymer is from about 5 mM to about 20 mM. In some embodiments, the concentration of nanoparticles is from about 0.1% (v/v) to about 1.0% (v/v).

In some embodiments, the biosensors further comprise a biological polymer of interest conjugated to a target moiety, wherein the target moiety has high affinity for the capture moiety. The biological polymer of interest may comprise any polynucleotide, polypeptide, or polysaccharide that is capable of binding to, hybridizing to, or reacting with a biological or chemical molecule of interest. Examples of biological or chemical molecules of interest include, but are not limited to, polynucleotides, polypeptides, sugars, hormones, metabolites, toxins, microbes, vitamins, and metal ions.

In some embodiments, the biological polymers of interest are polynucleotides that are capable of binding to or hybridizing to protein or nucleic acid biomarkers of interest. In some embodiments, the biological polymers of interest are aptamers that are capable of binding to protein biomarkers. In some embodiments, the biological polymers of interest are oligonucleotides that are capable of hybridizing to nucleic acid biomarkers. In some embodiments, the biological polymers of interest are proteins (e.g., antibodies) that are capable of binding to protein biomarkers. The biological polymers of interest, e.g., oligonucleotides, aptamers, and/or antibodies, can bind to nucleic acid or protein biomarkers or a fragment thereof. For example, an oligonucleotide capture moiety can bind to a nucleic acid biomarker that is a genomic DNA sequence, for example one or more exons or introns, or a portion of exonic or intronic sequence that is at least 10, 15, 20, 25, 50, 100, or more nucleotides in length, or a mRNA sequence that is at least 10, 15, 20, 25, 50, 100, or more nucleotides in length. An aptamer or antibody capture moiety can bind to a protein biomarker that is a full-length protein, a truncated protein, or a fragment thereof, for example one or more regions or domains of the protein.

The polymer-based biosensors of the present invention are universal platforms that may be adapted for the detection of any biomarker of interest, for example for the detection of biomarkers that indicate the presence of a cancer, disease, or condition. In an exemplary embodiment, the biosensors detect protein and nucleic acid biomarkers that indicate the presence of an oral disease such as oral cancer. Interleukin-8 (IL) RNA, IL-8 protein, and IL-1β protein are three biomarkers for the detection of the oral cancer oral squamous cell carcinoma (Wong, J. Am. Dent. Assoc. 137:313-321 (2006)). As described herein in the Examples section, biosensors comprising antibodies against IL-8 or IL-1β or an oligonucleotide sequence against IL-8 RNA were generated that were able to detect IL-8 or IL-1β protein concentration or IL-8 RNA concentration with a level of sensitivity several orders of magnitude higher than is possible using sensors comprising abiotic polymers and abiotic nanoparticles.

Antibody and oligonucleotide reagents that can be used to detect expression levels of oral cancer biomarkers are known to those skilled in the art. Moreover, oligonucleotide reagents for detecting oral cancer biomarkers are disclosed in International Patent Application Number PCT/US2005/005263, filed on Feb. 17, 2005, and in International Patent Application Number PCT/US2008/081378, filed on Oct. 27, 2008, both hereby incorporated by reference for all purposes.

The target moiety may comprise any molecule that has affinity for (i.e., is capable of specifically binding to or specifically being bound by) a capture moiety of the nanoparticles of the present invention, such as small molecules, polypeptides, and polynucleotides. As used herein, "specifically binding to" or "specifically being bound by" refers to a level of binding of the target moiety binding to or being bound by the capture moiety that is at least two times over background and more typically more than 5 to 100 times or more over background. In some embodiments, the target moiety comprises an antigen, an antibody, an oligonucleotide, a receptor, a biotin, or a streptavidin. In an exemplary embodiment, the capture moiety comprises a streptavidin molecule or an anti-biotin antibody, and the target moiety comprises a biotin molecule.

IV. Methods of Making Polymer-Based Biosensors

In another aspect, the present invention provides for methods of making polymer-based biosensors as described herein, the method comprising the steps of: (a) doping a solution of monomeric units of a conducting polymer with negatively charged nanoparticles comprising a capture moiety; and (b) polymerizing the monomeric units on the surface of a sensor comprising an electrode, thereby trapping the nanoparticles on the surface of the sensor. In some embodiments, the method further comprises the step of: (c) contacting the polymerized surface with a biological polymer of interest conjugated to a target moiety, wherein the target moiety has high affinity for said capture moiety.

Polymerization of the monomeric units of the conducting polymer and the negatively charged nanoparticles comprising a capture moiety is typically accomplished by electropolymerization. Electropolymerization of the conducting polymer and nanoparticle is applied to the working electrode, but not the counter electrode or the reference electrode, such that the nanoparticle is immobilized specifically on the working electrode. Methods of electropolymerization are known to those skilled in the art and described in, e.g., Schuhmann et al., *Biosens. Bioelectron.* 12:1157-1167 (1997), incorporated herein by reference for all purposes. In an exemplary embodiment, the monomeric units of the conducting polymer and the negatively charged nanoparticles comprising a capture moiety are electropolymerized on the working electrode of a sensor comprising a plurality of three-electrode systems with a designed spiral structure, using a simple electrical polymerization process without the requirements for a clean room or lithographic processes.

The polymerization pattern can be visualized using any suitable imaging method. For imaging purposes, the biosensor is incubated with a target moiety conjugated to a detectable moiety. A wide variety of detectable moieties can be used, with the choice of label, depending on the sensitivity required, stability requirements, and available instrumentation and disposal provisions. Suitable detectable moieties include, but are not limited to, radionuclides, fluorescent dyes (e.g., fluorescein, fluorescein isothiocyanate (FITC), Oregon Green®, rhodamine, Texas Red®, tetrarhodimine isothiocynate (TRITC), Cy3®, Cy5®, ATTO® fluorescent dyes, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, metals, and the like. A signal from the detectable moiety can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength.

In an exemplary embodiment, the patterning of the biosensor is visualized using fluorescence imaging. The sensor, comprising nanoparticle comprising streptavidin or anti-biotin capture moieties, is incubated with Atto-488®-labeled biotin and visualized by fluorescent microscopy. Using fluorescent microscopy, it is possible to visualize the direct polymerization patterns of the conducting polymer and nanoparticle on the surface of the working electrode.

The amount of surface coverage and the distribution of the binding sites, or capture moieties, on the surface of the sensor may be controlled by varying the polymerization time of the conducting polymer/nanoparticle solution on the surface of the sensor. As described herein in the Examples, a short polymerization time results in nanoparticles having low surface occupancy and random orientation on the surface of the sensor. As the polymerization time increases, surface coverage of the nanoparticles increases monotonically. The surface morphology of the sensor may be characterized by microscopy, e.g., scanning electron microscopy.

The thickness of the polymerized biosensor can be measured by profilometry (e.g., the Dektak® 6 Surface Profile Measuring System, Veeco). The thickness of the polymerized biosensor can vary based on differences in potential during electropolymerization, and the thickness of the polymerized biosensor affects the electrochemical response and signal-to-background ratio of the biosensor. For each biosensor, the ideal thickness may vary based on the geometry and material of the electrode, and therefore the optimal voltage conditions may need to be separately determined for each type of electrode that is used.

V. Methods of Detecting Analytes Using Polymer-Based Biosensors

In another aspect, the present invention provides for methods of detecting analytes in a solution, the method comprising: contacting the solution with a polymer-based biosensor as described herein; applying a voltage to the electrode; and determining the current generated on the biosensor.

The analyte to be detected may comprise any biological or chemical molecule of interest, including but not limited to proteins, nucleic acids, vitamins, metabolites, metal ions, toxins, etc. The analyte may be obtained from any biological sample, including blood, saliva, tissue, cultured cells (e.g., primary cultures, explants, and transformed cells), stool, urine, etc. In some embodiments, the analyte is obtained from a saliva sample. In some embodiments, the saliva sample is obtained from a human. The analyte may be in any solution that conducts an electrical signal. In some embodiments, the analyte is obtained from a biological sample and diluted in a solution of phosphate-buffered saline.

In some embodiments, the analyte is a biomarker for a disease or condition. In some embodiments, the analyte is a protein biomarker or a nucleic acid biomarker. In some embodiments, the analyte is a biomarker that is differentially expressed in a subject having a disease or condition, and the method further comprises detecting the amount of analyte present in the subject and comparing the amount to an amount of analyte present in a control, wherein an amount of analyte present in the subject that is higher or lower than the amount present in the control indicates the presence of the disease or condition. In some embodiments, the analyte is a biomarker that is differentially expressed in a subject having an oral disease such as oral cancer.

In an exemplary embodiment, the analytes to be detected are biomarkers for oral cancer, wherein the biomarkers are IL-8 protein, IL-8 RNA, and IL-1β protein analytes in human saliva samples. Probes binding or hybridizing to the biomarker of interest (e.g., an anti-IL-8 antibody that binds IL-8 protein, a hairpin oligonucleotide sequence that hybridizes IL-8 RNA, or an anti-IL-1β antibody that binds IL-1β protein) are conjugated to a target moiety that binds the capture moiety of the nanoparticle on the surface of the biosensor, the probes are applied to the working electrode of the biosensor, and the entire biosensor is contacted with the solution comprising the analyte of interest.

Detection of analytes in a solution can be accomplished using any of a number of detection methods, including but not limited to, amperometric detection, immunoassay, electrochemical impedance spectroscopy, fluorescence spectroscopy, quartz crystal microbalance, and surface plasmon resonance. Optionally, amplification of the signal can be enhanced by preceding detection with a signal amplification step. Multiple folds of amplification of the probe density on the surface of the biosensor result in, for example, enhanced intensity if using fluorescent spectrometry, more weight increase if using quartz crystal microbalance, bigger shift of resonance wavelength if using surface plasmon resonance, and increased current readout if using enzymatic amperometry. In some embodiments, detection of the analyte is accomplished by amperometric detection combined with immunoassay, in which the probe-bound analyte is amplified through immunoassay before amperometric detection.

In some embodiments, signal amplification is accomplished using an HRP-conjugated moiety capable of binding to the probe that is immobilized on the biosensor. In an exemplary embodiment, the probe is a biotin- and FITC-labeled hairpin oligonucleotide that is immobilized to the surface of the biosensor, to which horseradish peroxidase (HRP) conjugated to anti-FITC antibody is applied. In the absence of an analyte that binds the hairpin oligonucleotide probe, the HRP-conjugated anti-FITC does not bind the probe due to steric hindrance, resulting in a low background signal. However, binding of analyte to the probe changes the conformation of the probe and removes the steric hindrance, allowing the HRP-conjugated anti-FITC to bind the probe and resulting in increased signal output. See, e.g., Wei et al., *Nucleic Acids Res.* 36:e65 (2008); Wei et al., *Langmuir* 22:6280-6285 (2006); and Wei et al., *J. Am. Chem. Soc.* 127:5306-5307 (2005), all incorporated herein by reference for all purposes. Signal amplification can be further modified by varying the length or structure of the oligonucleotide probe, thereby changing the separation distance between the probe and the surface of the biosensor.

Using the polymer-based biosensors described herein, the sensitivity of analyte detection is several orders of magnitude better than analyte detection using an abiotic polymer and abiotic nanoparticle. In some embodiments, the limit of detection of protein using the methods of the present invention is about 100 femtomolar. In some embodiments, the detection range for protein using the methods of the present invention is from about 100 femtomolar to about 2.5 micromolar. In some embodiments, the limit of detection of RNA using the methods of the present invention is about 10 attomolar. In some embodiments, the detection range for RNA using the methods of the present invention is from about 10 attomolar to about 10 picomolar.

The methods described herein may be adjusted in order to increase the dynamic range of detection for the polymer-based biosensor, for example by altering the amounts of detection reagents or the length of incubation time. In some embodiments, detection can be made more sensitive by applying a small amount of primary/secondary antibody and long time passive incubation time. In some embodiments, detection can be made less sensitive by applying an increased amount of primary/secondary antibody and short time active incubation time under an electrical field were applied.

VI. Compositions, Kits, and Integrated Systems

The invention provides compositions, kits, and integrated systems for practicing the detection methods described herein using antibodies specific for the polypeptides or nucleic acids specific for the polynucleotides of the invention.

Kits for carrying out the detection assays of the invention typically include a probe that comprises an antibody or nucleic acid sequence that specifically binds to polypeptides or polynucleotides of the invention, conjugated to a target moiety that can bind to or be bound by a capture moiety of the nanoparticle on the polymer-based biosensor. The kits may include several antibodies or polynucleotide sequences encoding polypeptides of the invention, e.g., a cocktail of antibodies that recognize the proteins encoded by the biomarkers of the invention.

VII. EXAMPLES

The following examples are offered to illustrate, but not to limit, the claimed invention.

Herein, we demonstrate that the combination of abiotic polymer substrate and bionanoparticle generates a biocompatible and widely applicable interface for detectors with multiple applications. In this example, poly(pyrrole) was chosen as the abiotic conducting polymer material because it is a commonly used polymer and can be very easily fabricated through electropolymerization. DNA dendrimer was chosen as the bionanoparticle. DNA dendrimer has the advantage of excellent stability, and because it is negatively charged, it effectively incorporates into a conducting polymer. Furthermore, DNA dendrimers can be customized to accommodate binding sites for small molecules, such as biotin and fluoroscein. Multiple binding sites, 5-1000 on each dendrimer particle, are expected to significantly increase the density of immobilized biomolecules. The properties of such an interface were tested with DNA dendrimer-linked nucleic acid and antibody through biosensing applications.

Example 1

Surface Patterning of DNA Dendrimer-Ppy by Electropolymerization

When an electrochemical bio-sensor is used, the target molecules need to be immobilized specifically on the working electrode (WE) but not on the counter electrode (CE) or the reference electrode (RE) (Gau, J. J. et al., *Biosensors & Bioelectronics*, 16:745-755 (2001); Gau, V. et al., *Methods*, 37:73-83 (2005); Gau, V. J. J. et al., *Pediatric Research*, 53:324A-324A (2003)). Most commonly, a lithographic process needs to be applied to pattern the capture probes onto WE. For the DNA dendrimer-poly(pyrrole) (DDPpy)-based sensor platform, target molecules can be patterned on the WE by a simple electrical polymerization process without multiple steps of blocking and lithographic processes. The formation of DDPpy is illustrated in FIG. 1A. The DNA dendrimer was pre-labeled with streptavidin or anti-biotin antibody and then mixed with non-labeled pyrrole monomer. By applying voltage across the WE and CE, the DNA dendrimer-guided polypyrrole is polymerized only on WE and not elsewhere within 5 minutes. The process was carried out in a typical laboratory environment without the requirement of a clean room and laborious lithographic processes.

Figures 2A, 2B:
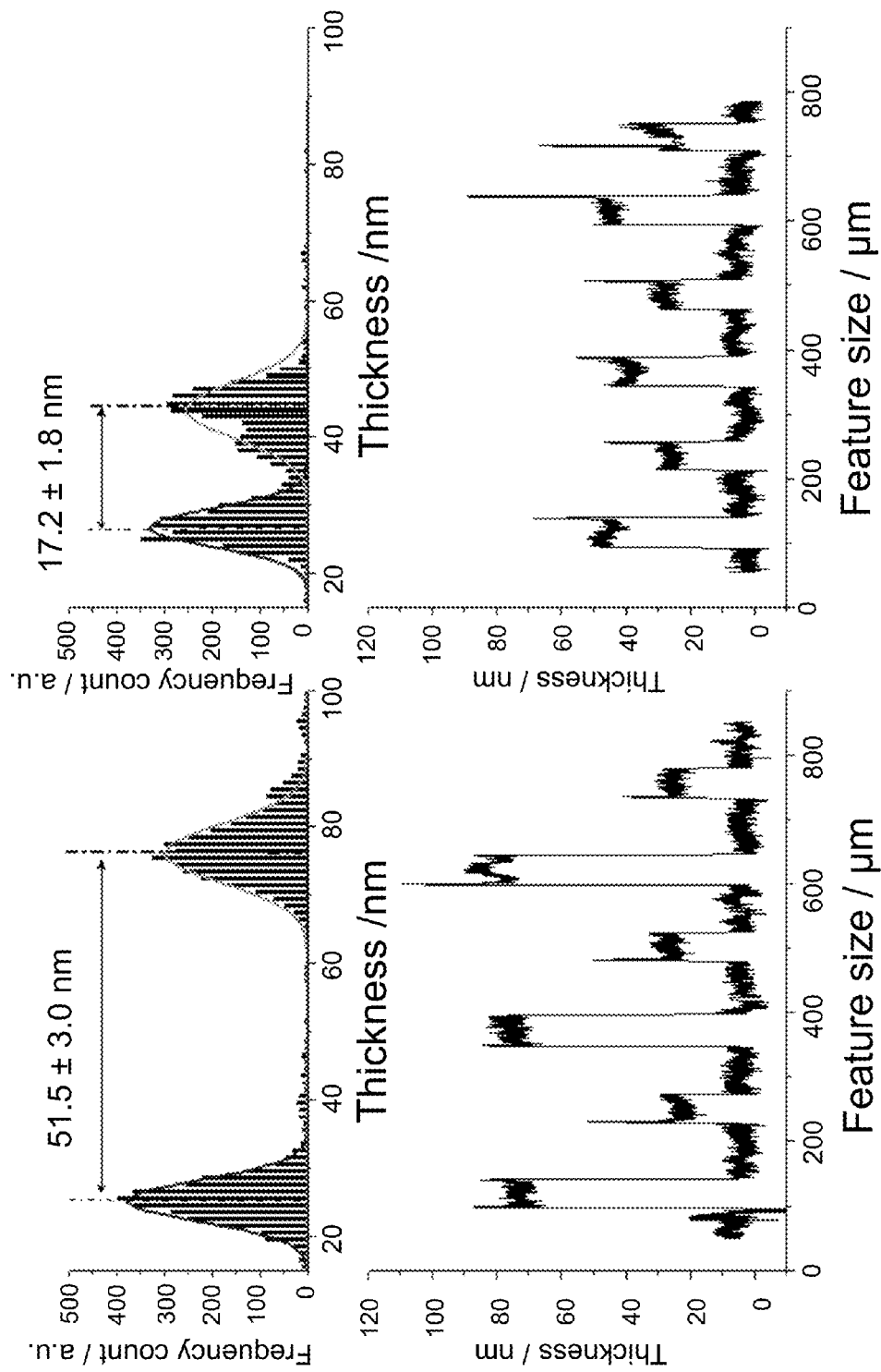
FIG. 2. Thickness analysis of (A) DDPpy film and (B) Ppy film. By fitting the thickness distribution with Gaussian profile, DDPpy thickness under electric pulse for 500 s was determined to be 51.5±3.0 nm, while thickness of Ppy only film under electric pulse for 500 s was 17.2±1.8 nm.

The thickness of the DDPpy film was measured by comparing the thickness of the WE with that of the CE, since the polymer film is localized on the WE. The thickness measurement was done by profilometer (Dektak 6 Surface Profile Measuring System, Veeco). For each specific polymerization condition, triplicate measurements were carried out. By fitting the thickness distribution with a Gaussian profile, DDPpy thickness under electric pulse for 500 s was determined to be 51.5±3.0 nm, while the thickness of Ppy-only film under electric pulse for 500 s was 17.2±1.8 nm (FIG. 2). The effect of DDPpy thickness was carefully studied. Different potential during electropolymerization results in different thickness. High voltage results in thick film and dark color. The electrochemical response increases as the thickness increases, both for specifical signal and blank control. However, considering the signal-to-background ratio (SBR), there exists an optimized thickness for the sensor. Both thick film and thin film have poor SBRs compared with film of the optimal thickness. The relationship between electropolymerization, film thickness, and sensor responses is illustrated in Table 1. For the DDPpy film described in this example, the optimal condition was determined to be +350 mV/+950 mV in polymerization, resulting in a film thickness of 51.5±3.0 nm. However, the optimal condition depends on the geometry and material of the electrode. For each type of electrode, the optimal condition may need to be determined separately.

TABLE 1

DDPpy film thickness and sensor response under different electropolymerization conditions.

| | Potential in electrochemical polymerization | Thickness (nm) | Current (nA) at 2.5 µg/ml | Current (nA) at blank |
|---|---|---|---|---|
| 1 | +350 mV/+550 mV | 8.4 ± 0.7 | −343.9 ± 11.2 | −10.1 ± 1.5 |
| 2 | +350 mV/+750 mV | 31.3 ± 2.0 | −997.5 ± 28.2 | −12.7 ± 0.8 |
| 3 | +350 mV/+950 mV | 51.5 ± 3.0 | −2260.7 ± 259.9 | −16.8 ± 2.7 |
| 4 | +350 mV/+1150 mV | 108.4 ± 9.4 | −2897.2 ± 391.5 | −223.3 ± 29.1 |

Figure 3:
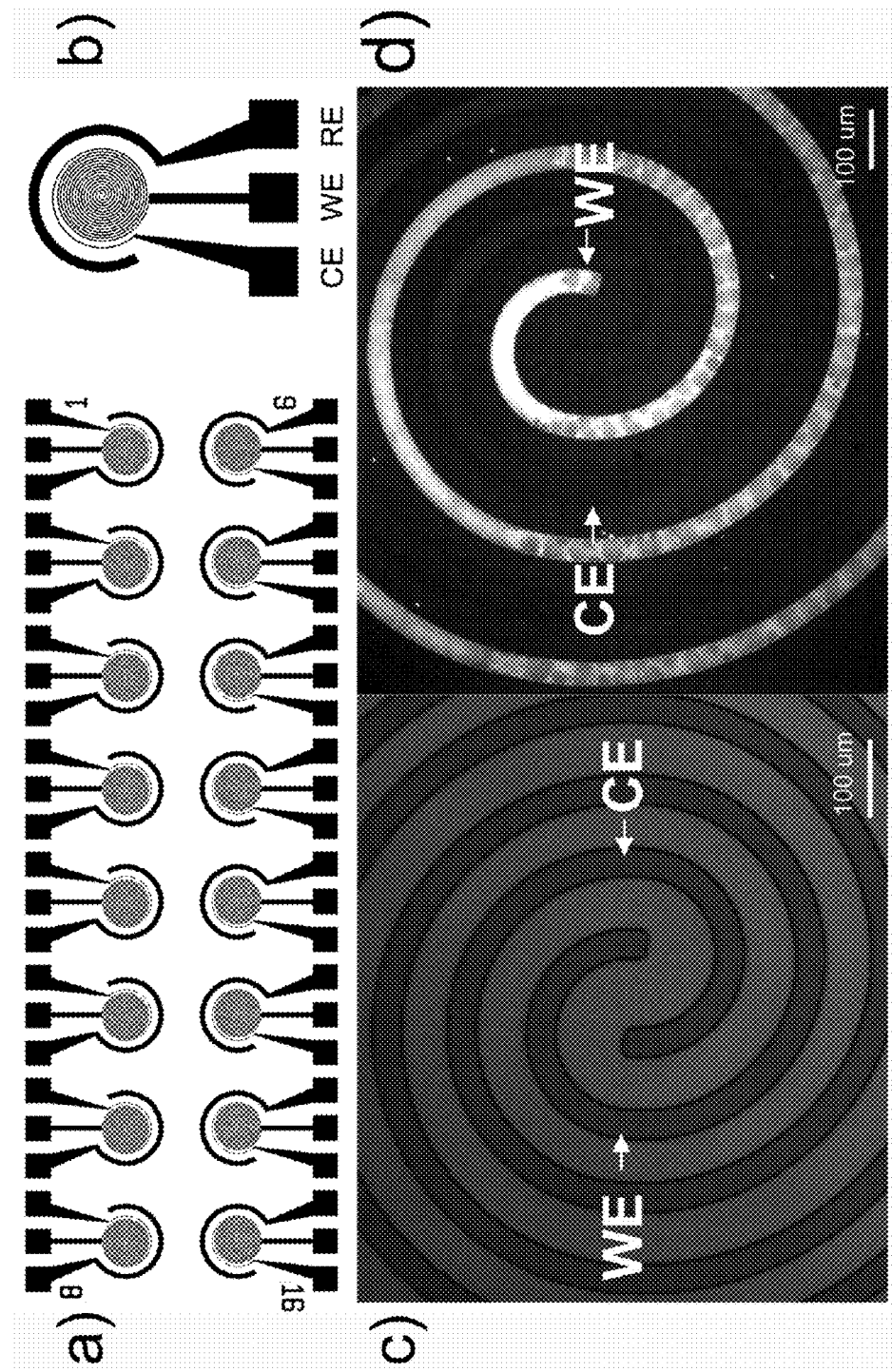
FIG. 3. Patterning of DDPpy by an electrical field. A. 16-array electrochemical chip. B. Three-electrode configuration of each array. The size of the total 16-array chip is 2.5×7.5 cm2. C-D. Bright-field image (C) and fluorescence image (D) of the DDPpy working electrode (WE) and bare gold counter electrode (CE) after incubation with biotinylated Atto-488.

DDPpy is electro-polymerized on WE of a 16-array chip with a designed spiral structure (FIG. 3A-B). This simple patterning process of DDPpy on WE can be visualized by using fluorescence imaging. The DDPpy sensor chip is incubated with Atto-488®-labeled biotin. The bright-field image of the DDPpy electrode is shown in FIG. 3C and the fluorescence image is shown in FIG. 3D. The WE shows a 10 times higher fluorescent signal on average 20 than those of the CE and glass substrate. Based on the high contrast and the sharp edge of the fluorescent images, direct polymerization patterns of DDPpy on WE and the activity of the streptavidin are well maintained.

By placing droplets with either biotinylated antibody or nucleic acid probes on the islands, an array of sensors can be fabricated for detecting a variety of different targeted molecules (FIG. 1B).

Example 2

Controlling the Dendrimer Surface Density in DDPpy

Figure 4:
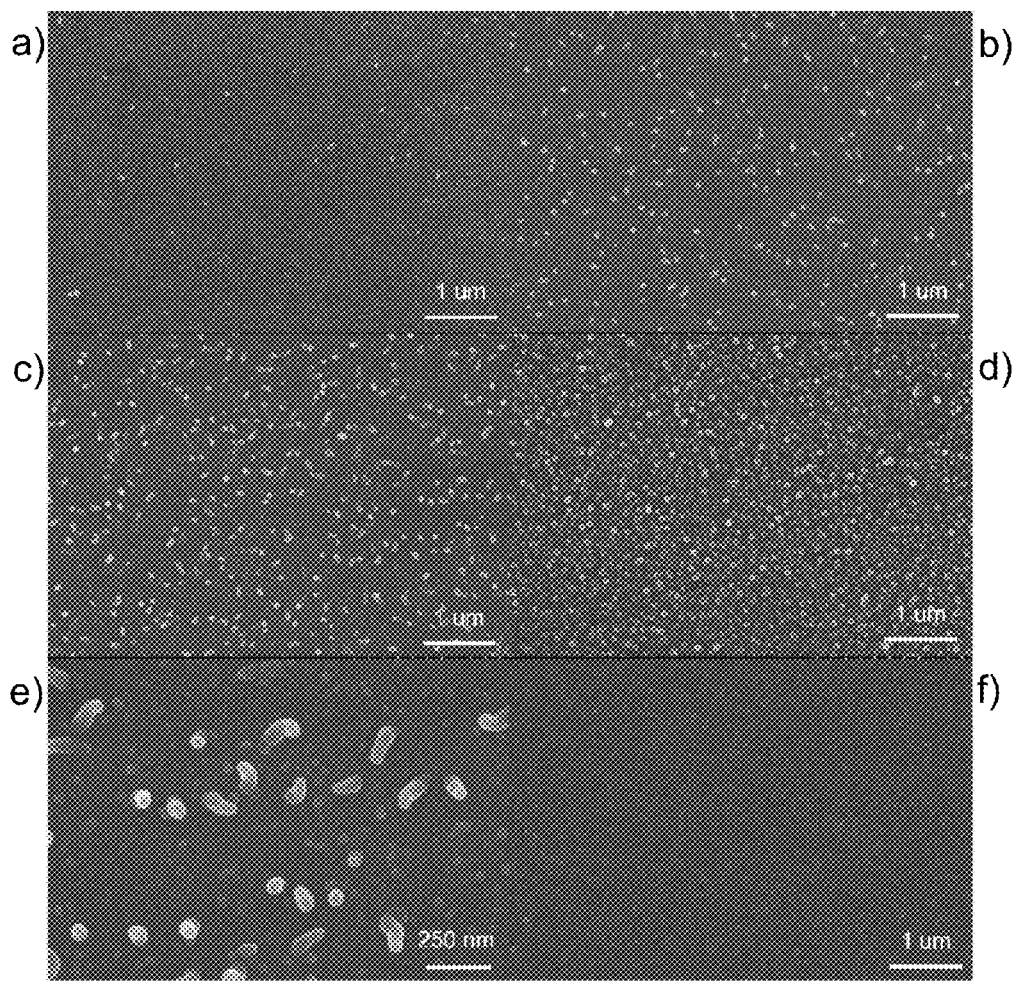
FIG. 4. SEM images of the DDPpy surface and Ppy-only surface. A-D. DDPpy after polymerization for 50, 150, 300, and 500 s, respectively, with 20 k magnification. E. DDPpy after polymerization for 300 s with 70 k magnification. F. Ppy after polymerization for 500 s with 20 k magnification.

Surface morphology and coverage of the binding sites affect the performance of surface immobilized molecular sensors. Sparsely distributed molecules result in a low number of binding targets, whereas very crowded surfaces would restrict the recognition process because of the limited free space (Lee, C. Y. et al., *Analytical Chemistry*, 79:4390-4400 (2007)) and generate low surface binding efficiency (Ricci, F. et al., *Langmuir*, 23:6827-6834 (2007); Peterson, A. W. et al., *Journal of the American Chemical Society*, 124:14601-14607 (2002); Popp, D. et al., *Journal of Molecular Biology*, 368: 365-374 (2007); Bonanno, L. M. and DeLouise, L. A., *Langmuir*, 23:5817-5823 (2007)). The surface density of binding sites is directly proportional to the concentration of DNA dendrimer in the polypyrrole matrix. We can effectively control the number and distribution of the binding sites by an appropriate duration of electropolymerization of the DNA dendrimer. A series of experiments on different polymerization time have been performed and the data are summarized in Table 2. Scanning electron microscopy (SEM; Hitachi S4700 SEM, Japan) was used to characterize the surface morphology and coverage of DDPpy. For short polymerization times (FIGS. 4A-B), the dendrimer particles have low surface occupancy and random orientations. As the polymerization time increases (FIGS. 4C-D), surface coverage increase monotonically. The surface density of the exposed dendrimer can be controlled by varying the duration of electro-polymerization. At high magnification (FIG. 4E), the image shows that dendrimer particles tend to adopt an upright orientation. Since the electropotential is perpendicular at the surface, the negatively charged DNA dendrimer aligns its orientation (Lee, C. Y. et al., *Analytical Chemistry*, 79:4390-4400 (2007); Calonder, C. et al., *Journal of Biomedical Materials Research Part A*, 75A:316-323 (2005); Vikholm, I. and Albers, W. M., *Langmuir*, 14:3865-3872 (1998); Chung, J. W. et al., *Journal of Biotechnology*, 126:325-333 (2006); Boozer, C. et al., *Langmuir*, 22:4694-4698 (2006)). The average particle size is calculated to be 60-80 nm, which is very close to the value provided by the dendrimer manufacturer. Assuming that a monolayer of DNA dendrimer is exposed on a Ppy surface (FIG. 4F), the surface density of the dendrimer is about 1.2 pmol/cm$^2$ after 500 s of square-wave electropolymerization.

TABLE 2

Parameters measured in surface characterization of a DDPpy electrode

| Polymerization time [s] | Particle diameter [nm] | Surface coverage [%] | Surface concentration$^a$ [pmol/cm$^2$] |
|---|---|---|---|
| 50 | 40 | 0.5 | 0.02 |
| 150 | 62 | 5.5 | 0.24 |
| 300 | 78 | 8.5 | 0.35 |
| 500 | 70 | 35.2 | 1.21 |

$^a$The surface concentration is calculated from the percentage of surface coverage and the average particle size under the assumption of a monolayer of DDPpy film. This assumption is supported by a film thickness of 50 nm.

Example 3

Applications in Biomolecular Sensing

Amperometric detection combined with sandwich immunoassay is a robust method to detect low concentrations of analytes (Wang, J. and Jiang, M., *Langmuir*, 16:2269-2274 (2000)). Here, we used a dendrimer that is embedded in conducting polymer (CP) to establish an interface for facilitating the transduction from biochemical reactions to electronic output signals.

To demonstrate the efficiency of the bio/abiotic interface, a combination of salivary biomarkers, interleukin-8 (IL-8) RNA, IL-8 protein, and IL-1β protein, was used in the buffer. These three markers have been proven to be able to specifically detect oral cancer (Wong, D. T., *Journal of the American Dental Association*, 137:313-321 (2006)). The levels of these biomarkers in oral cancer patients are significantly higher than those in healthy people, and can therefore be used as a reference to screen such patients. As reported, the average concentrations of IL-8 and IL-1β proteins in oral cancer patients are about several thousand pg/ml but less than several hundred pg/ml in healthy subjects (Li, Y. et al., *Clinical Cancer Research,* 10:8442-8450 (2004)). However, for each individual, the level of protein marker may vary from pg/ml to ng/ml for both cancer patients and the control group. Thus, salivary protein sensors will be needed to provide a quantitative response in this wide range, and high sensitivity with a limit of detection (LOD) of sub-pg/ml. For IL-8 mRNA, the average level in cancer patients is about 16 fM and is 2 fM for healthy people. Again, for each individual, the level in clinical sample ranges from attomoles to several picomoles. The requirement for the dynamic range is from attomoles to picomoles and the LOD would therefore be in sub-femtomole range.

Figure 5:
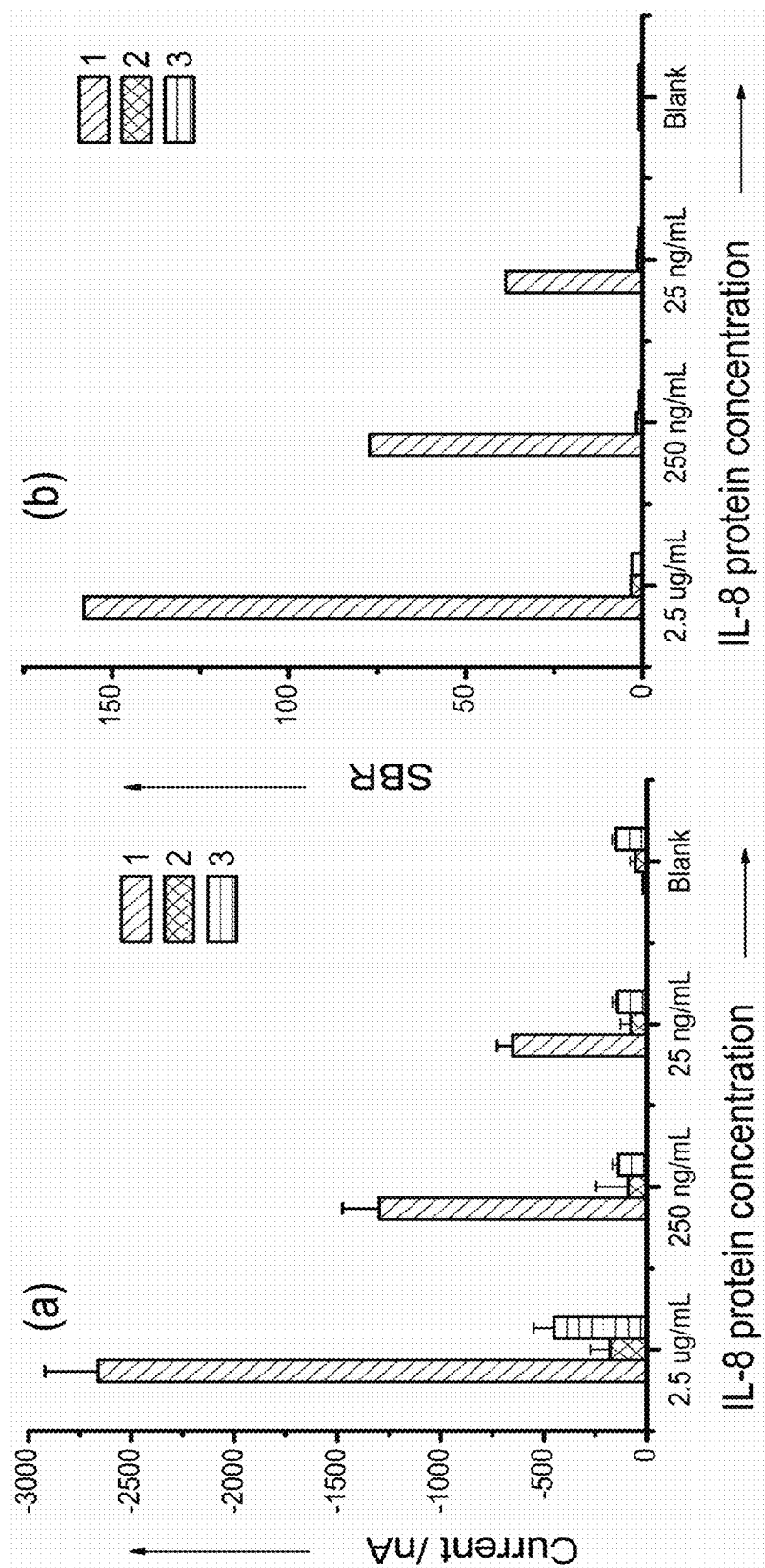
FIG. 5. Signal comparison. Signal comparison of (A) electrochemical data and (B) signal-to-background ratio (SBR) from amperometric IL-8 protein assays by applying a (1) DDPpy sensor, (2) Ppy-only sensor, or (3) direct covalent bond without polymer.

The first experiment illustrates the necessity for the CP. On a gold electrode, proteins will experience denaturing problems. The interfacial polymer film can prevent this conformational change in the proteins. Due to a low efficiency in encapsulating the neutral protein into the CP, the sensor without the interfacial polymer has a higher signal level than that of Ppy-only sensor (FIG. 5). However, the background noise of the bare sensor is high and indicates denatured protein on the gold surface. The LOD of the Ppy sensor is in the low ng/ml range, whereas that of the bare sensor is only in the low µg/ml range. These results indicate that the CP is an effective interface material for maintaining the activity of the proteins on sensor surface.

To demonstrate the improved interfacial property by adding dendrimer to Ppy, comparative immunoassays between Ppy-only and DDPpy sensors were carried out in parallel. In the control experiments with a Ppy-only film, biotinylated monoclonal antibody (Mab) was directly doped into the polymer film by using the same parameters as in DDPpy formation. As the results in FIG. 5 show, DDPpy immunosensors exhibit much higher output signals than the Ppy sensor under the same target concentration. At 2.5 µg/ml of IL-8 target protein, DDPpy sensors generate about 15 times higher current (−2660 nA) than in the dendrimer-free case (−176 nA). In addition, the signal of the blank control on DDPpy is −17 nA, which is much lower than the −55 nA of the Ppy sensor, indicating that DDPpy also resists nonspecific protein adsorption. In terms of signal-to-background ratio (SBR), DDPpy sensors achieved a SBR as high as 38 with an IL-8 concentration of 25 ng/ml, while Ppy sensor only produced a SBR of 1.4 (FIG. 5B). Moreover, repeatability of these two surfaces is also different. Regarding the signal error level, on average DDPpy immunosensors result in a signal variation of 1-2 nA in the same batch and 3-4 nA between batches. Variations for Ppy sensors are noticeably larger, 3-4 nA, within the batch and >20 nA between batches. These results suggest that the dendrimer, the bio/abiotic interface in DDPpy immunosensor, plays a significant role in enhancing the sensitivity and repeatability.

Figure 6:
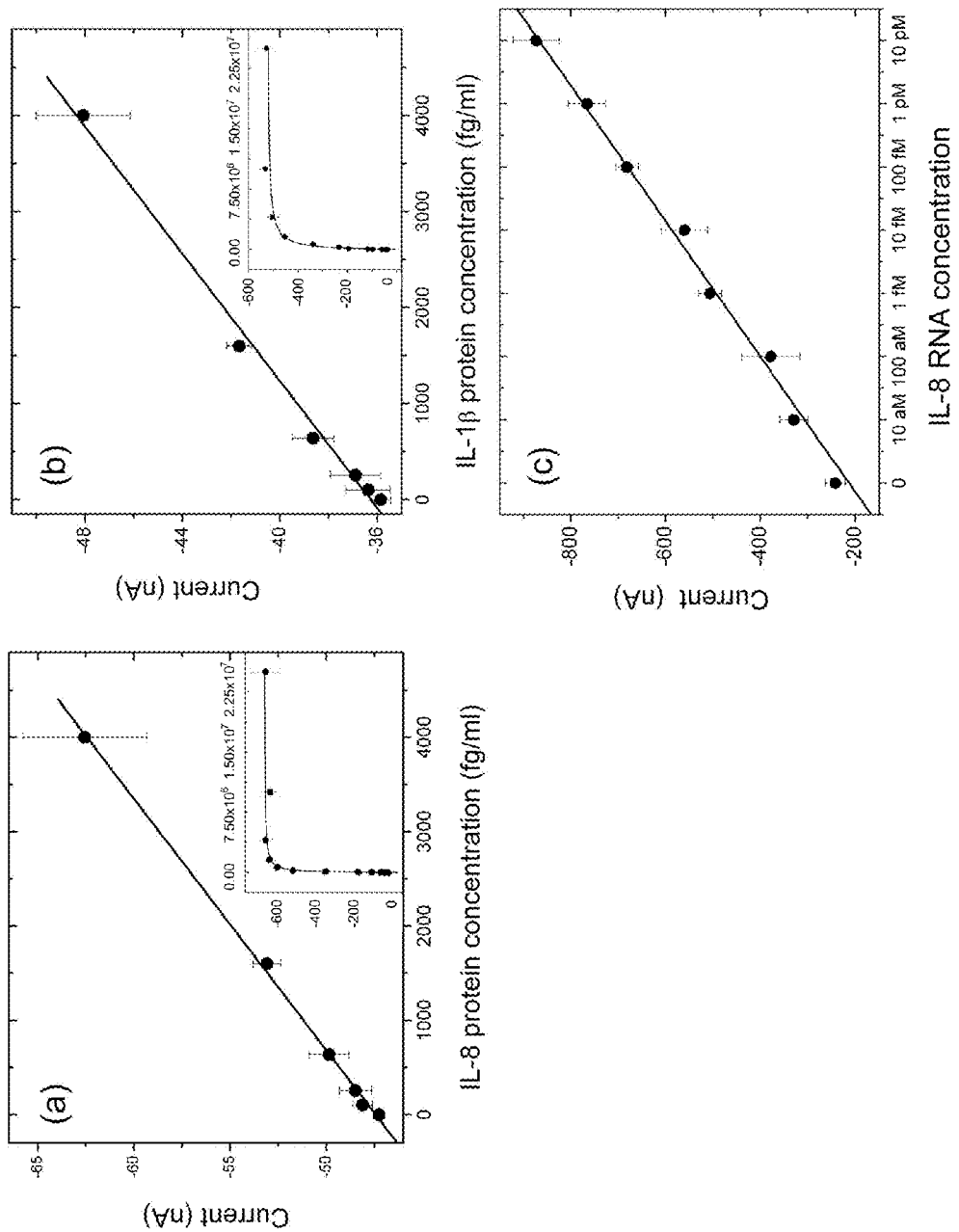
FIG. 6. Concentration profiles for the detection of salivary biomarkers using a streptavidin-labeled DDPpy biosensor. Concentration profiles obtained by plotting amperometric current intensities versus concentration of (A) IL-8 protein ($R^2$=0.99 for low concentration), (B) IL-1β protein ($R^2$=0.99 for low concentration), and (C) IL-8 RNA ($R^2$=0.98) with the linear fit results. The sensor responses from 0 to 25 ng of IL-8 and IL-1β are shown in the insets of (A) and (B), respectively, fitted with the Langmuir isotherm.

FIGS. 6A and B illustrate the linear concentration profiles for the detection of IL-8 and IL-1β protein in the low concentration range using streptavidin-labeled DNA dendrimer-Ppy sensors. The LOD was about 200 fg/ml for IL-8 protein and 100 fg/ml for IL-1β protein, which were about three orders of magnitude better than that of Ppy-only sensor. For concentrations in the range from 0 to 25 ng/ml, Langmuir isotherm profiles were observed (insets of FIGS. 6A and B). The amperometric response I has the following relationship with concentration c:

$$I = I_{saturate} \frac{Kc}{1+Kc},$$

where K is the binding constant which relates to the surface binding equilibrium. Regarding the multiple-layer-based surface recognition process, a complex Langmuir curve may exist at a high concentration range, especially for a protein surface. In our experiment, multiple layers followed the Langmuir equation or a more complex surface model was observed. Here, we only looked at the single Langmuir isotherm of the first monolayer (less than 25 ng/ml for IL-8 and IL-1β protein). According to the single Langmuir isotherm, the fitting results are as follows:

For IL-8 protein, $K=1.0\pm0.2\times10^{-5}$ (fg/ml)$^{-1}$ ($9.5\pm1.1\times10^{10}$ M$^{-1}$, MW=8 kD)

For IL-1β protein, $K=4.2\pm0.9\times10^{-6}$ (fg/ml)$^{-1}$ ($7.5\pm1.5\times10^{10}$ M$^{-1}$, MW=17.4 kD)

where MW is the molecular weight. The binding constant K from curve fitting is close to the $1/k_d$ between Mab and antigen in solution, which indicates that the DDPpy film maintains the bioactivity of the protein on the surface by constructing the bio/abiotic interface.

Figure 7:
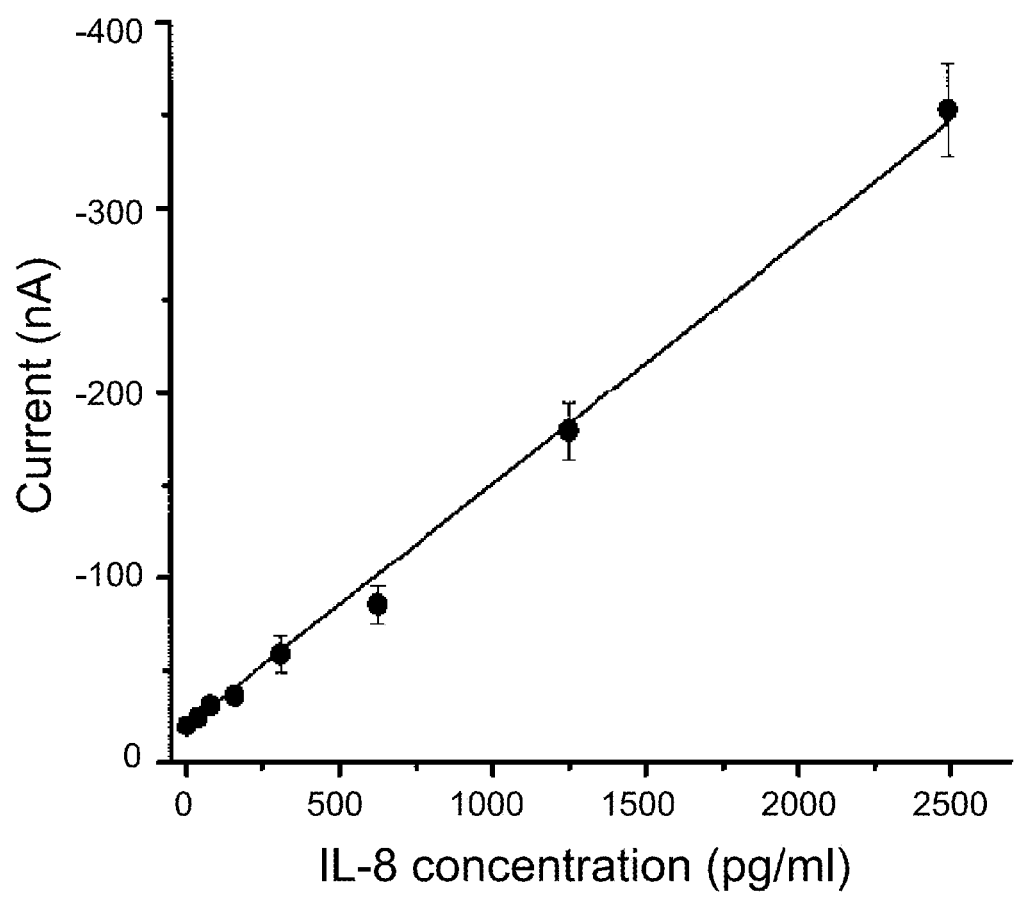
FIG. 7. Concentration profile for the detection of IL-8 protein using an anti-biotin-labeled DDPpy biosensor. Concentration profile of IL-8 protein plotted against current intensity with the linear fit results.

FIG. 7 illustrates the linear concentration profiles for the detection of IL-8 protein in the low concentration range using anti-biotin antibody-labeled DNA dendrimer-Ppy sensors. Electrochemical current intensities exhibited a very good linear relationship (R=0.99) with a corresponding concentration of IL-8 from 20 pg/ml to 2500 pg/ml in the buffer. The LOD was determined to be as low as 20 pg/mL in the total volume of 4 µL, which is equal to about 10 attomole IL-8 molecules. These results, from both the anti-biotin antibody-labeled and the streptavidin-labeled DNA dendrimer-Ppy sensors, indicate that DDPpy amperometric bioassay meets the requirements of point-of-care detection of proteins such as IL-8 and IL-1β for salivary diagnostics.

In addition to proteins, other molecular probes, such as oligonucleotides, can be immobilized efficiently through specific conjugation with DDPpy. Using a hairpin DNA probe to provide the hybridization selectivity, IL-8 mRNA (NM_000584), another salivary biomarker for oral cancer, was detected using an anti-biotin antibody-labeled or a streptavidin-labeled DNA dendrimer-Ppy sensor. The signal amplification was achieved by applying horseradish peroxidase (HRP) and 3,3',5,5'-tetramethylbenzidine (TMB)/$H_2O_2$. By immobilizing the hairpin probe on the DDPpy surface, the steric hindrance effect inhibits the binding of HRP conjugate to the target-free probe (Wei, F. et al., *Nucleic Acids Research,* doi:10.1093/*nar/gkn*299 (2008)), resulting in a very low background signal. Therefore, the distance between the surface and reporter label of the probe will be a major factor in the detection process (Wei, F. et al., *Langmuir,* 22:6280-6285 (2006); Wei, F. et al., *Journal of the American Chemical Society,* 127:5306-5307 (2005)). Upon target binding, the reporter is removed from the surface into the solution. Therefore the restriction by the surface is diminished. Conjugated HRP binds to fluorescein and the current signal output will then increase above the background level.

Figure 8:
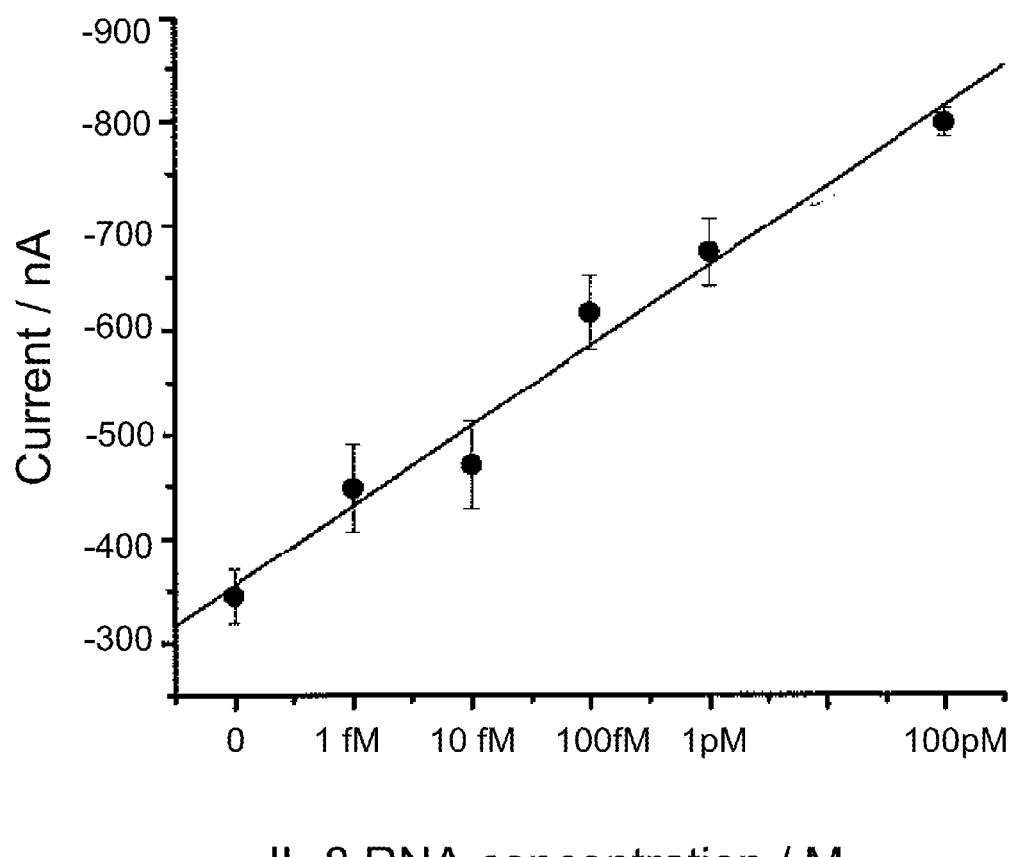
FIG. 8. Concentration profile for the detection of IL-8 RNA using an anti-biotin-labeled DDPpy biosensor. Concentration profile of IL-8 RNA plotted against current intensity with the linear fit results.

Using the streptavidin-labeled DNA dendrimer-Ppy sensor, we were able to detect IL-8 RNA with a large dynamic range from 10 aM to 10 pM (FIG. 6C). Most significantly, the LOD of the RNA was about 10 aM with 4 µl of sample (about 40 ymol or 25 copies) in a buffer system. Using the anti-biotin antibody-labeled DNA dendrimer-Ppy sensor, we developed an effective method of electrochemical detection of RNA with large dynamic range from fM to nM, as shown in FIG. 8. Significantly, the current LOD of conducting polymer sensor is about 5 fM for short DNA/RNA fragments (Fan, Y. et al., *Journal of the American Chemical Society,* 129:5437-5443 (2007); Jiang, C. et al., *Electrochimica Acta,* 53:2917-2924 (2008)), even by abiotic nanoparticles without this bio/abiotic interface.

The above results demonstrate the ability of DDPpy sensor for high sensitivity and wide dynamic range. Furthermore, the dynamic range of the DDPpy sensor could be adjusted by changing the recognition surface. In the application for ultrasensitive detection, a small amount of primary/secondary antibody and long time passive incubation time are applied. To move the dynamic range to a high concentration, an increased amount of primary/secondary antibody and short time active incubation time under an electrical field were applied. With the modified protocol, the linear range covers from pg/ml to several hundred ng/ml (data not shown).

Discussion

From the comparison between sensors with pyrrole only or with a DNA-dendrimer-bridged pyrrole interface, DDPpy film exhibits much better bioaffinity and higher specificity for detecting immobilized proteins. The LOD of the current bio/abiotic interfaced DDPpy sensor is better than that of sensors with interfaces of abiotic nanoparticles and abiotic polymer (Fan, C. H. et al., *Proceedings of the National Academy of Sciences of the United States of America,* 100:6297-6301 (2003); Jiang, C. et al., *Electrochimica Acta,* 53:2917-2924 (2008)). These results indicate that the bio/abiotic interface greatly improves the signal transduction process.

In addition, the bio/abiotic interface provides wide possibilities for a flexibly designed sensor. The interfacial film embedded with DNA dendrimer has multiple binding sites that can be labeled with multiple types of probes. In this work, biotinylated protein and RNA served as the target molecules, and thus streptavidin-labeled DNA dendrimer or anti-biotin antibody-labeled DNA dendrimer was selected. Since the basic units of DNA dendrimer are oligonucleotides, tags other than streptavidin or anti-biotin antibody can be conjugated with the DNA dendrimer. The labeling for the biomolecule target is therefore not limited to biotin. Additionally, one DNA dendrimer could be constructed by many varieties of oligonucleotides with different tags, and the DNA dendrimer composition could be synthesized according to the needs of multiple types of target detections.

For a CP-based sensor, the electrical-field-assisted polymerization simplifies the surface patterning process not only for the abiotic polymer, but also for the bionanodopant particles, DNA dendrimer. If only one type of DNA dendrimer is used, the nanoparticles can be mixed with CP and patterned at the same time. If different types of DNA dendrimer are needed for multiplexing detections, the negatively charged nanoparticles can be patterned at desired sensors sequentially. The time scale for each step is from several seconds to several minutes.

In addition to the Ppy used in this Example, the CP could be made of various kinds of CP, such as poly(3,4-ethylenedioxythiophene) (PEDOT) (Kros, A. et al., *Sensors and Actuators B-Chemical,* 106:289-295 (2005)). The supporting substrate is not limited to be gold, but rather can be substituted by other conducting or semiconducting material, such as platinum, indium tin oxide, and silicon.

Figure 9:
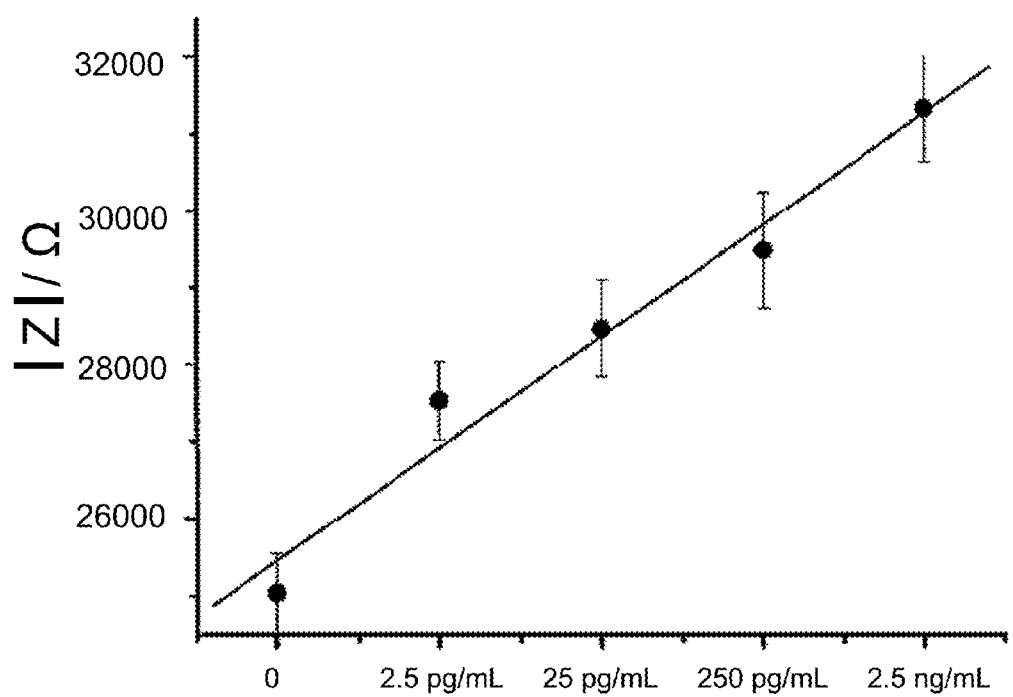
FIG. 9. Detection of IL-8 protein by electrochemical impedance spectroscopy. Concentration profile of IL-8 protein plotted against impedance modulus intensity with the linear fit results.

Many other detection methods other than electrochemical sensing are applicable to the DDPpy platform. For example, due to the electrical conductivity of the CP, surface binding of a specific target will change charge distribution on DDPpy interface and block exposed CP surface, resulting in prominent change of charge transfer resistance between electronic mediator and CP covered electrode. This change can be quantitatively recorded via electrochemical impedance spectroscopy (EIS) as a label-free detection method. FIG. 9 shows detection of IL-8 protein using EIS. Briefly, biotinylated anti-IL-8 mAb was loaded onto the DDPpy surface. After incubation with a series of concentrations of IL-8 samples, sensors were directly characterized by potentiostatic EIS at OV vs. open circuit potential (EOC) in the frequency range of 100 kHz-1 Hz. A concentration profile was then obtained by plotting modulus of impedance at 10 Hz vs. corresponding IL-8 concentration. The resulting LOD was as good as a few ng/ml, which is among the best results for label-free protein detection that have been reported in literature.

Experimental Section

Surface Fabrication of DNA-Dendrimer-Directed Ppy Electrodes

DNA dendrimer, conjugated to either streptavidin or anti-biotin antibody, was purchased (Genisphere, USA) For the streptavidin-labeled dendrimer, each dendrimer was 70-90 nm in diameter with two to four streptavidin units. For the anti-biotin antibody-labeled dendrimer, each dendrimer was 70-90 nm in diameter with two to four antibodies. For electropolymerization, the dendrimer was diluted with 1×PBS (pH 7.5, Invitrogen, USA) in the volume ratio of 1:200 and with pyrrole (Sigma, USA). The final pyrrole concentration was about 10 mM. The electrodes were immersed in the mixture before electropolymerization.

The pattern of chips composed of 16 sets of three-electrode systems was designed and fabricated via photolithography (FIGS. 3A-B). After the glass substrate was thoroughly cleaned, a 5 nm thick of Ti layer and 20 nm of Au were evaporated onto the glass sequentially.

Figure 10A:
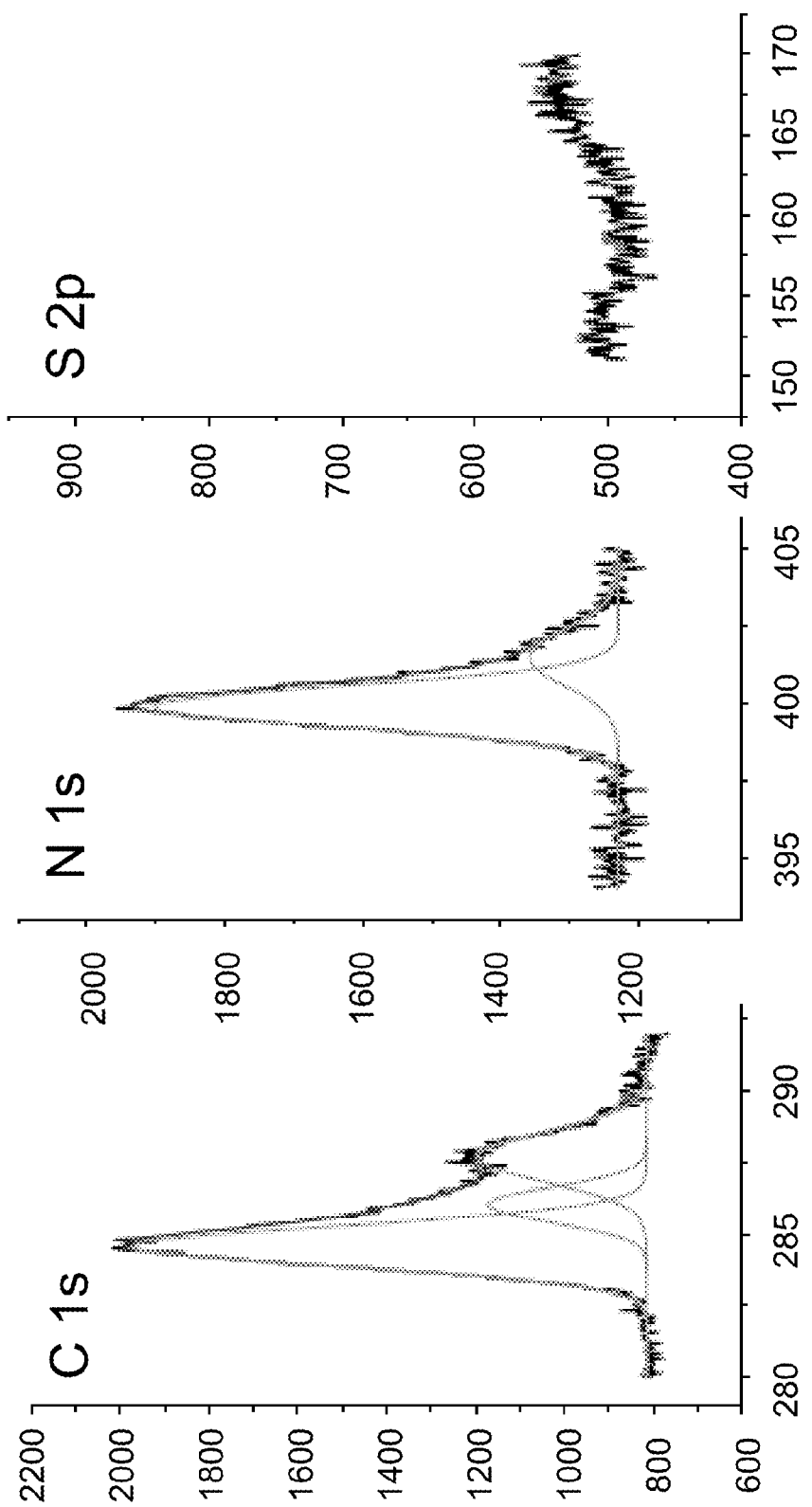
FIG. 10. X-ray photoelectron spectra (XPS). XPS of (A) Ppy film only, (B) DDPpy film only, (C) DDPpy film after biotinylated IL-8 antibody binding.
Figure 10B:
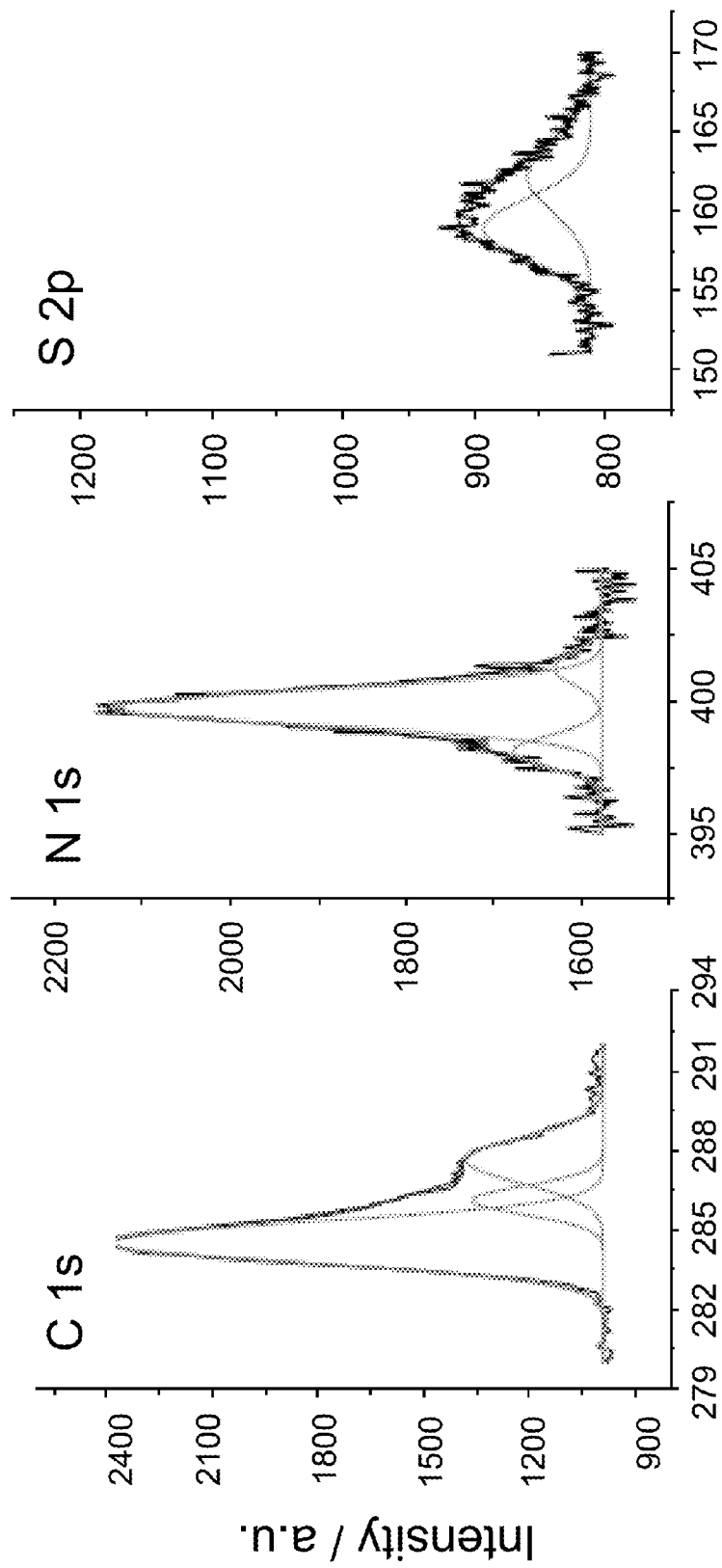
Figure 10C:
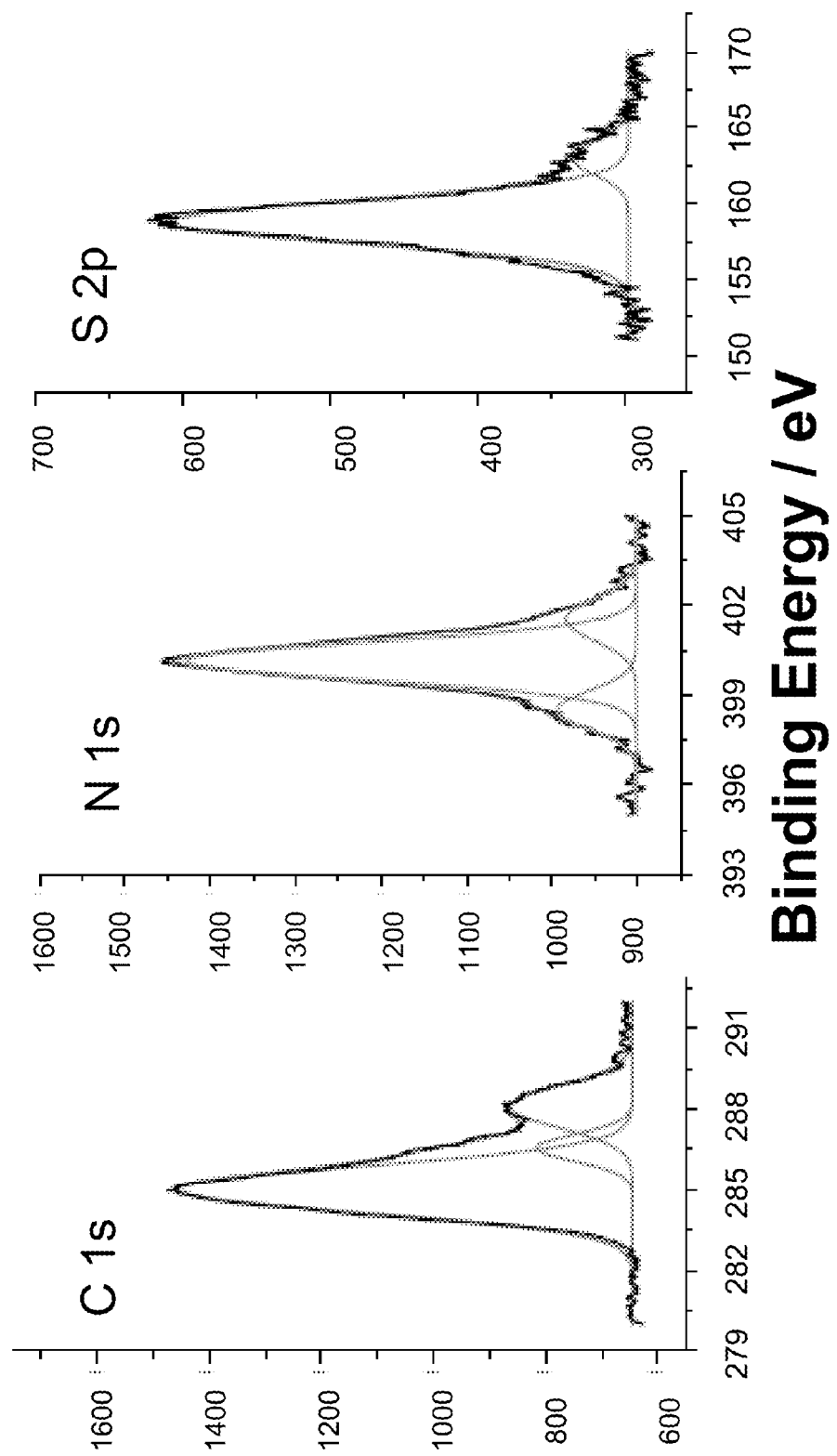

A cyclic square-waveform electrical field was used for electro-polymerization [Schuhmann, W. et al., *Biosensors & Bioelectronics,* 12:1157-1167 (1997)]. For the streptavidin-labeled DDPpy biosensors, each square-wave cycle consisted of 9 s at the potential of +350 mV and 1 s at +950 mV, and 20 square-wave cycles were applied in total; the whole process lasted for 200 s. For the anti-biotin antibody-labeled DDPpy biosensors, each square-wave cycle consisted of 9 s at the potential of +350 mV and 1 s at +950 mV, and 50 square-wave cycles were applied in total; the whole process lasted for 500 s. After polymerization, the electrode was rinsed with ultra pure water (18.3 MΩ·cm) then dried by pure $N_2$. The effects of DDPpy thicknesses to the signal-to-background level were carefully studied. Under the optimized conditions, the thickness of the polymer film was measured in triplet mode by a profilometer (Dektak 6 Surface Profile Measuring System, Veeco) to give a value of is 51.5±3.0 nm. X-ray photoelectron spectra (XPS) measurements were performed in the analysis chamber of an Omicron XPS/UPS system. The base pressure of the chamber was better than $10^{-9}$ mbar. Al Kα (1486.6 eV) was used as the excitation source. As shown in FIG. 10, C 1 s, N 1 s, and S 2 p were observed for three types of polymer films. From the DDPpy film after protein binding (FIG. 7C), S 2 p occupied two peaks at 158.8 eV and 163.6 eV, which are designated to the —SH from the side chain of peptides and —S—S in the protein, respectively. N 1 s exhibits 3 peaks at 398.5 eV (=N—), 400.0 eV (—NH—), and 401.1 eV (—$N^+$—). The =N— and —NH— are from the nucleic acid in DNA-dendrimer units. The —NH— and —$N^+$— were most likely contributed by the polypyrrole matrix. This was supported by the 286.6 eV in C 1 s spectra component. For DDPpy only film, S 2 p peak was observed, due to the streptavidin from the DNA dendrimer. The =N—, —NH—, and —$N^+$— peaks are also detected in DDPpy film. For Ppy only film, no S 2 p signal was detected. The N 2 s spectra only show 400.0 eV (—NH—) and 401.1 eV (—N⁺—) which come from the pyrrole backbone.

Immunoassay

For protein detection, biotinylated human IL-8/IL-1β monoclonal antibody (Mab) (0.01 mg/ml, 4 µl; Pierce, USA) in 1×PBS was loaded onto electrodes to be conjugated with the streptavidin dendrimer. The incubation time was 30 min followed by washing and drying. Human IL-8/IL-1β (4 µl; Pierce) in different concentrations was loaded onto the DDPpy-Mab surface, and was diluted by the standard diluent from the Pierce IL-8/IL-1β kit for enzyme-linked immunosorbent assay (ELISA). The incubation time was 30 min, followed by washing and drying. After this step, if testing by EIS, the impedances measurements (CHI 660A, multichannels, USA) were instantly carried out in a buffer containing 3,3',5,5' tetramethylbenzidine substrate (TMB/$H_2O_2$, low activity) (Neogen, USA). |Z| at 10 Hz was read out and then plotted against IL-8 concentration. For amperometric detection, an extra incubation was required: secondary HRP-conjugated human IL-8/IL-1β Mab (1:100, 4 µl) was added for 30 min in the HRP dilution buffer from the Pierce IL-8 ELISA kit, and after washing and drying, TMB/$H_2O_2$ substrate was loaded and amperometric detection was carried out by applying a potential of −200 mV to each electrode unit, followed by parallel signal readout after equilibration for 60 s. All the potentials were referred to Au reference electrode (gold RE). The gold reference electrode was determined to be +218 mV versus the saturated calomel electrode (SCE) by measuring cyclic voltammetric curves of 0.1 mM [Fe(CN)$_6$]$^{3-/4-}$ (Gau, V. et al., *Methods*, 37:73-83 (2005)). In all the steps, the solutions were loaded onto the whole area of micropatterned electrode region, including working electrode and counter electrode.

mRNA Detection

After the polymerization of the electrode, biotin (10 nM) and fluorescein isothiocyanate (FITC) dual-labeled hairpin probe (4 µl; Operon, USA) in 1XTris-HCl was loaded onto the electrode to be conjugated with the streptavidin dendrimer. The hairpin sequence was GAGGGTTGC TCA GCC CTC TTC AAA AAC TTC TCC ACAACCCTC (SEQ ID NO: 1), which was calculated based on MFold (SantaLucia, J., Proceedings of the National Academy of Sciences of the United States of America, 95:1460-1465 (1998); Zuker, M., Nucleic Acids Research, 31:3406-3415 (2003)). The chip was washed and dried after 30 min of incubation. Then in vitro transcript IL-8 RNA (4 µl) in different concentrations was loaded onto the hairpin probe-coated surface. The hybridization buffer was 1XTris-HCl containing 10 mM $MgCl_2$. Another 30 min of incubation was required, followed by washing and drying. To generate specific signal amplification for hybridized oligonucleotide, secondary HRP conjugated with anti-FITC antibody (4 µl) was incubated with the electrodes for 30 min and the chip was washed and dried. Lastly, measurements were carried out with the same parameters as in amperometric protein detection.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of detecting an analyte in a solution, the method comprising the steps of: (a) contacting the solution with a polymer-based biosensor, wherein the biosensor comprises a conducting polymer and a negatively charged nanoparticle, wherein the conducting polymer comprises a poly (pyrrole) and the negatively charged nanoparticle comprises a DNA dendrimer comprising a capture moiety capable of binding to the analyte and configured for amperometric detection; (b) applying a voltage to the biosensor; (c) determining a current intensity generated on the biosensor; and (d) detecting the presence or absence of the analyte in the solution, wherein the current intensity generated on the biosensor is linearly dependent on the amount of the analyte in the solution.

2. The method of claim 1, wherein the analyte is a protein.

3. The method of claim 2, wherein the protein is present at a concentration of between about 100 fg/mL to about 2.5 µg/mL.

4. The method of claim 1, wherein the analyte is a nucleic acid.

5. The method of claim 4, wherein the nucleic acid is present at a concentration of between about 10 aM to about 10 pM.

6. The method of claim 1, wherein the solution comprises a bodily fluid.

7. The method of claim 6, wherein the bodily fluid is saliva.

8. The method of claim 1, wherein the analyte is an oral cancer biomarker.

9. The method of claim 8, wherein the oral cancer biomarker is selected from the group consisting of interleukin (IL)-8 protein, IL-1β protein, and IL-8 mRNA.

10. The method of claim 1, wherein the capture moiety is selected from the group consisting of an oligonucleotide, polypeptide, antibody or functional fragment thereof, an avidin, a streptavidin, a biotin, an aptamer, a L-RNA aptamer, a glutathione, an S-peptide, and an anti-biotin antibody.

* * * * *